(12) United States Patent
Nakasaki et al.

(10) Patent No.: US 7,999,356 B2
(45) Date of Patent: Aug. 16, 2011

(54) COMPOSITION FOR FILM FORMATION, INSULATING FILM, SEMICONDUCTOR DEVICE, AND PROCESS FOR PRODUCING THE SEMICONDUCTOR DEVICE

(75) Inventors: Yasushi Nakasaki, Yokohama (JP); Nobuhide Yamada, Yokkaichi (JP); Miyoko Shimada, Yokohama (JP); Hideshi Miyajima, Yokohama (JP); Kei Watanabe, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 96 days.

(21) Appl. No.: 12/548,492

(22) Filed: Aug. 27, 2009

(65) Prior Publication Data
US 2010/0072581 A1 Mar. 25, 2010

(30) Foreign Application Priority Data
Sep. 25, 2008 (JP) ................... 2008-246845

(51) Int. Cl.
*H01L 23/58* (2006.01)
(52) U.S. Cl. ...................... 257/632; 438/790
(58) Field of Classification Search .................. 556/431; 438/790; 257/632, E29.006, E21.24
See application file for complete search history.

(56) References Cited

FOREIGN PATENT DOCUMENTS

| JP | 11186996 | 1/2001 |
|---|---|---|
| JP | 2001096678 | 10/2002 |
| JP | 2001098183 | 10/2002 |
| JP | 2001140275 | 11/2002 |
| JP | 2002359239 | 12/2002 |
| JP | 2001388109 | 7/2003 |
| JP | 3718709 | 9/2005 |
| JP | 2006111738 | 4/2006 |
| JP | 2006241304 | 9/2006 |
| JP | 2007119488 | 5/2007 |
| JP | 2006176041 | 1/2008 |

OTHER PUBLICATIONS

N. Tajima et al., Carbon-Rich SiOCH Films With Hydrocarbon Network Bonds For Low-k Dielectrics: First-Principles Investigation, IEEE International Interconnect Technology Conference, 2006, pp. 122-124.
N. Tajima et al., Carbon-Doped Silicon Oxide Films With Hydrocarbon Network Bonds For Low-k Dielectrics: Theoretical Investigations, Japanese Journal Of Applied Physics, 2007, vol. 46, No. 9A, pp. 5970-5974.
T. Takahashi et al., A Convenient One-Pot Procedure To Arylcyclobutenes From Arylacetylenes, J. Org. Chem., 1999, vol. 64, pp. 8706-8708.

*Primary Examiner* — Matthew W Such
*Assistant Examiner* — Monica D Harrison
(74) *Attorney, Agent, or Firm* — Turocy & Watson, LLP

(57) ABSTRACT

According to one aspect of the present invention, there is provided a composition for film formation, comprising a compound represented by general formula (I) or a hydrolyzed-dehydrocondensation product thereof:

$$X^1_{3-m}R^1_m SiR^2 SiR^3_n X^2_{3-n} \quad (I)$$

wherein $R^1$ and $R^3$ represent a hydrogen atom or a monovalent substituent; $R^2$ represents a divalent group having an alicyclic structure with four carbon atoms or a derivative of the divalent group; $X^1$ and $X^2$ represent a hydrolysable group; and m and n are an integer of from 0 to 2.

14 Claims, 21 Drawing Sheets

COMPOSITION FOR FILM FORMATION, INSULATING FILM, SEMICONDUCTOR DEVICE, AND PROCESS FOR PRODUCING THE SEMICONDUCTOR DEVICE

CROSS-REFERENCE TO RELATED APPLICATIONS

This application is based upon and claims the benefit of priority from the prior Japanese Patent Applications No. 2008-246845, filed on Sep. 25, 2008; the entire contents of which are incorporated herein by reference.

BACKGROUND

1. Technical Field

Disclosure generally relates to a composition for film formation, an insulating film, a semiconductor device, and a process for producing the semiconductor device.

2. Background Art

Silica ($SiO_2$) films formed by vacuum processes such as chemical vapor deposition (CVD) have hitherto been commonly used as interlayer insulating films, for example, in semiconductor devices. However, even for CVD-$SiO_2$ films having the lowest relative permittivity (i.e. dielectric constant k) among inorganic material films, the dielectric constant is about 4. The dielectric constant of SiOF films, which have been developed as CVD films with low-permittivity (low-k), is about 3.3 to 3.5. The SiOF films, however, are highly hygroscopic, and the its dielectric constant disadvantageously increases over time of use.

In recent years, coating-type insulating films, composed mainly of a hydrolyzed-dehydrocondensation product of a tetraalkoxysilane (TEOS), called SOG (spin-on-glass) films are also being used with a view to forming more uniform interlayer insulating films. Here, the hydrolyzed-dehydrocondensation means a dehydrocondensation reaction between hydrolyzed products.

Further, further integration in semiconductor devices and the like has led to the development of low-k interlayer insulating films, composed mainly of a polyorganosiloxane, called organic SOG. In particular, low-k interlayer insulating films, composed mainly of polymethylsilsesquioxane (in which dice-shaped silicas of $Si_8O_{12}$ have been crosslinked to each other via an oxygen atom in each cross-linkage, a part of cross-linkages having been replaced with a methyl group), called MSQ have also been developed.

The organosilicon oxide films have two structural features. One of them is that a part of cross-linkages has been converted to a hydrocarbon termination such as Si—$CH_3$, whereby the cross-linked structure is broken. The other feature is that a part of cross-linked structures by a Si—O—Si cross-linkage in silica has been replaced with cross-linked structures by a hydrocarbon cross-linkage (i.e. hydrocarbon cross-linked structure) such as Si—$CH_2$—Si or Si—$CH_2$—$CH_2$—Si. Breakage of the cross-linked structure results in the formation of cross-linkage-free gaps, that is, vacant spaces or pores having a dielectric constant of 1, in the insulating film. As a result, the dielectric constant of the whole film is decreased. Further, an increase in the proportion of the hydrocarbon cross-linked structure to the Si—O—Si cross-linkage also leads to an increase in the volume proportion of the cross-linkage-free gaps in the insulating film.

An increase in the proportion of cross-linkage-free gaps (pores), however, poses a problem that spaces, which are formed in a production process of semiconductor devices and the like, act as disadvantageous sites which absorb and hold various substances, that is, particularly moisture and an etching gases, from the outside of the films.

Under such circumstances, a method is known in which a material comprising an organopolysiloxane and high-boiling point solvents or thermally decomposable compounds added to the organopolysiloxane is used as an insulating film material having excellent insulating properties, heat resistance, and mechanical strength in order to form pores in the film and thus to lower the dielectric constant of the film.

The above porous film, however, suffers from problems, for example, that the pore formation lowers the dielectric constant but, at the same time, weakens the mechanical strength and, further, an increase in dielectric constant occurs disadvantageously due to moisture absorption into the pores. Further, since pores connected to each other are formed, copper atoms used for interconnections disadvantageously diffuse through the insulating film. That is, it is required that the pores should be effective for reducing the dielectric constant of the insulating film but each of them has a small pore volume and are not connected to each other.

However, the organosilicon oxide films, particularly when the thickness is large (about 1 mm) as that of the interlayer insulating film like the upper layers in the multilevel interconnect technology, cause cracking disadvantageously due to the intrinsic stress of the films per se and deteriorate resistance against CMP (chemical mechanical polishing). It has been confirmed as the stress corrosion cracking that the occurrence and progress of this cracking are accelerated by moisture introduced into the film by moisture absorption. However, it is very difficult to control inexpensively for keeping an external moisture content on a low level in all of semiconductor device manufacturing process environments after formation of low-k insulating film.

In order to solve the above problems, techniques for producing insulating films have been developed in which a compound produced by cross-linking Si atoms with straight-chain alkyl (normal alkyl) groups is used with a view to lowering the dielectric constant and improving the mechanical strength. These techniques, however, have never achieved enough the requirements for dielectric constant, mechanical strength and moisture absorption resistance of the films.

Further, a technique in which an organosilicon oxide film using a compound cross-linked by an aromatic or other alicyclic group is used, or a technique in which an organosilicon oxide film using an aromatic or other alicyclic group is used in a part of a cross-linkage has been developed (see, for example, JP-A 2006-241304 (KOKAI). Furthermore, a technique in which a disilacyclobutane structure (Si(—C—)$_2$Si) is used in a part of a cross-linkage has been developed (see, for example, JP-A 2006-111738 (KOKAI)). Even these techniques could not have satisfactorily met the requirements for dielectric constant, mechanical strength, and moisture absorption resistance of the films.

In these techniques, the number of carbon atoms contained in a cross-linkage moiety between silicon atoms, i.e., Si . . . Si, is disclosed to be from 1 to 50 in normal alkyl groups and is from 5 to 40 (preferably from 5 to 13) in a cyclic groups. Specifying the number of carbon atoms aims mainly at lowering the dielectric constant. The reason for this is as follows. Approximately two-thirds of the dielectric constant attributable to a siloxane skeleton of silica ($SiO_2$) is governed by oxygen (polarization of oxygen ion). Oxygen also functions to hold the film density on substantially the same level as that of polymorphic form of $SiO_2$ crystals by cross-linking between silicon (Si) atoms through oxygen. Cross-linking through carbon (I.e. hydrocarbons) is advantageous in that replacement of the oxygen with carbon can reduce the film density and can lower the polarizability of the film (both the electronic polarizability and the ionic polarizability).

However, material design guidelines based on clear-cut reasons for selecting the suitable number of carbon atoms in the cross-linkage moiety within the range from 1 to about 50, more specifically selecting a chemical structure (that is, cross-linkage structure) of these carbon atoms, and selection of materials according to the material design guidelines are not disclosed.

Of course, some precedent studies have been already reported on this guideline in IEEE International Interconnect Technology Conference, pp. 122-124, 2006 (reference 1) and Jpn. J. Appl. Phys., Vol. 46, No. 9A, pp. 5970-5974, 2007 (reference 2). In these references, a difference in potential energy curves for characteristic distortions (deformation potential curves) against external force applied to a cross-linkage moiety in interest is examined by computational simulations for cross-linkages by polymethylene groups in which the number of carbon atoms in the straight-chain alkyl (normal alkyl) group is in the range from 1 to 4, that is, four cross-linkage forms of $CH_2$ cross-linkage (methylene cross-linkage), $CH_2CH_2$ cross-linkage (ethylene cross-linkage), $CH_2CH_2CH_2$ cross-linkage (n-propylene cross-linkage), and $CH_2CH_2CH_2CH_2$ cross-linkage (n-butane cross-linkage). The results show two points that the dielectric constant decreases with increasing the number of $CH_2$ cross-linkage units, but on the other hand, the mechanical strength (Young's moduli) (i.e. the hardness) increases with decreasing the number of $CH_2$ cross-linkage units (i.e. decreasing the overall length of $CH_2$ cross-linkages). Consequently, the references have concluded that, due to the contradictory relationship between both properties with respect to the number of $CH_2$ cross-linkage units, $CH_2CH_2$ cross-linkage (ethylene cross-linkage) is the most suitable. According to the references, the reason why the mechanical strength increases with decreasing the number of $(CH_2)_n$ cross-linkage units is that the effect of restricting the deformation of relative positions between two Si atoms located at both ends of the cross-linkage is improved with decreasing the number of $(CH_2)_n$ cross-linkage units. That is, when the number of $(CH_2)_n$ cross-linkage units is smaller (i.e. the length of the overall length of $(CH_2)_n$ cross-linkage is shorter), the internal distortion energy is increased more rapidly against externally applied deformations, that is, the hardness is increased. However, the material design guidelines for the purposes of mechanical strength improvement in these references is entirely directed to an improvement in the skeleton strength of the film (an increase in Young's modulus).

In summary, the main purpose of conventional cross-linkage by a hydrocarbon group R (for example, a polymethylene group or a phenylene group) is to increase the hardness of the Si—R—Si skeleton (i.e., to increase tensile strength in a main chain direction, bending strength in a direction perpendicular to the main chain, or torsional strength around the main chain). The guiding principles in order to attain the purpose is that either the cross-linkage where the number of carbon atoms in Si—$(C)_n$—Si cross-linkage is increased or the cross-linkage where a planar structure of the benzene ring is utilized because of Si—C—Si cross-linkage being stiffer than Si—O—Si cross-linkage. Cross-linkages by carbon (C) are likely to be fixed against bending in a direction perpendicular to the main chain or torsion around the main chain because of the nature of either $sp^3$- or $sp^2$-hybrid orbitals of C. On the other hand, in cross-linkage by oxygen (O), the Si—O bond per se is also strong. Since, however, the O atom ordinarily has twofold coordination, the degree of freedom of rotation and torsional deformation around O is high enough that the O cross-linkages appear to be "flexible" ones.

Further, as described above, increasing the proportion of the hydrocarbon cross-linkages to the Si—O—Si cross-linkages leads to an disadvantageous increase in cross-linkage-free gaps (pores) and thus results in deteriorating moisture absorption resistance. In addition, an organosilicon oxide film having a high hydrocarbon content is similar, in a sense, to a resist material. Therefore, as the carbon content increases, resistance against reactive ion etching (RIE) for resist patterning processes and to resist ashing treatment (ashing) for resist removing processes is disadvantageously deteriorated.

To overcome the above problems, studies have also been made to apply plasma treatment using N- or H-containing gas instead of the conventional oxygen gas-containing RIE or ashing process. In this case, carbon is removed, for example, as HCN. The use of such gases, however, also suffers from the problem that a higher carbon content causes a more significant deterioration in resistance against plasma treatment.

SUMMARY

According to one aspect of the present invention, there is provided a composition for film formation, comprising a compound represented by general formula (I) or a hydrolyzed-dehydrocondensation product thereof:

$$X^1{}_{3-m}R^1{}_m SiR^2 SiR^3{}_n X^2{}_{3-n} \quad\quad (I)$$

wherein $R^1$ and $R^3$ represent a hydrogen atom or a monovalent substituent; $R^2$ represents a divalent group having an alicyclic structure with four carbon atoms or a derivative of the divalent group; $X^1$ and $X^2$ represent a hydrolysable group; and m and n are an integer of from 0 to 2. The divalent group represented by $R^2$ in general formula (I) represents cyclobutane ($-C_4H_6-$), cyclofluorobutane ($-C_4H_{6-X}F_X-$), cyclopolymethylbutane ($-C_4H_{6-X}(CH_3)_X-$), cyclopolymethylfluorobutane ($-C_4H_{6-Y-Z}(F_Y(CH_3)_Z)-$), cyclochlorobutane ($-C_4H_{6-X}Cl_X-$), or cyclopolymethylchlorobutane ($-C_4H_{6-Y-Z}(Cl_Y(CH_3)_Z)-$) wherein X is an integer of from 1 to 6; and Y and Z are an integer of from 1 to 5 and satisfy a relationship of $2 \leq Y+Z \leq 6$.

According to another aspect of the present invention, there is provided an insulating film comprising an organosilicon oxide film with a single-composition material or a multi-composition material fabricated using at least the above compositions for film formation.

According to still another aspect of the present invention, there is provided a semiconductor device comprising the above organosilicon oxide film According to a further aspect of the present invention, there is provided a process for producing a semiconductor device comprising the above organosilicon oxide film, wherein the organosilicon oxide film is formed by a process comprising: forming a film by a coating method or a plasma enhanced chemical vapor deposition method using at least the above compositions for film formation; annealing the film in an oxidizing atmosphere; and annealing the annealed film in a non-oxidizing atmosphere.

According to another aspect of the present invention, there is provided a process for producing a semiconductor device comprising the above organosilicon oxide film, wherein the organosilicon oxide film is formed by a process comprising: forming a film by a coating method or a plasma enhanced chemical vapor deposition method using the above compositions for film formation; and irradiating the film with an energy beam while annealing the film under the reduced pressure compared with an atmospheric pressure.

DETAILED DESCRIPTION

First Embodiment

Figure 1:
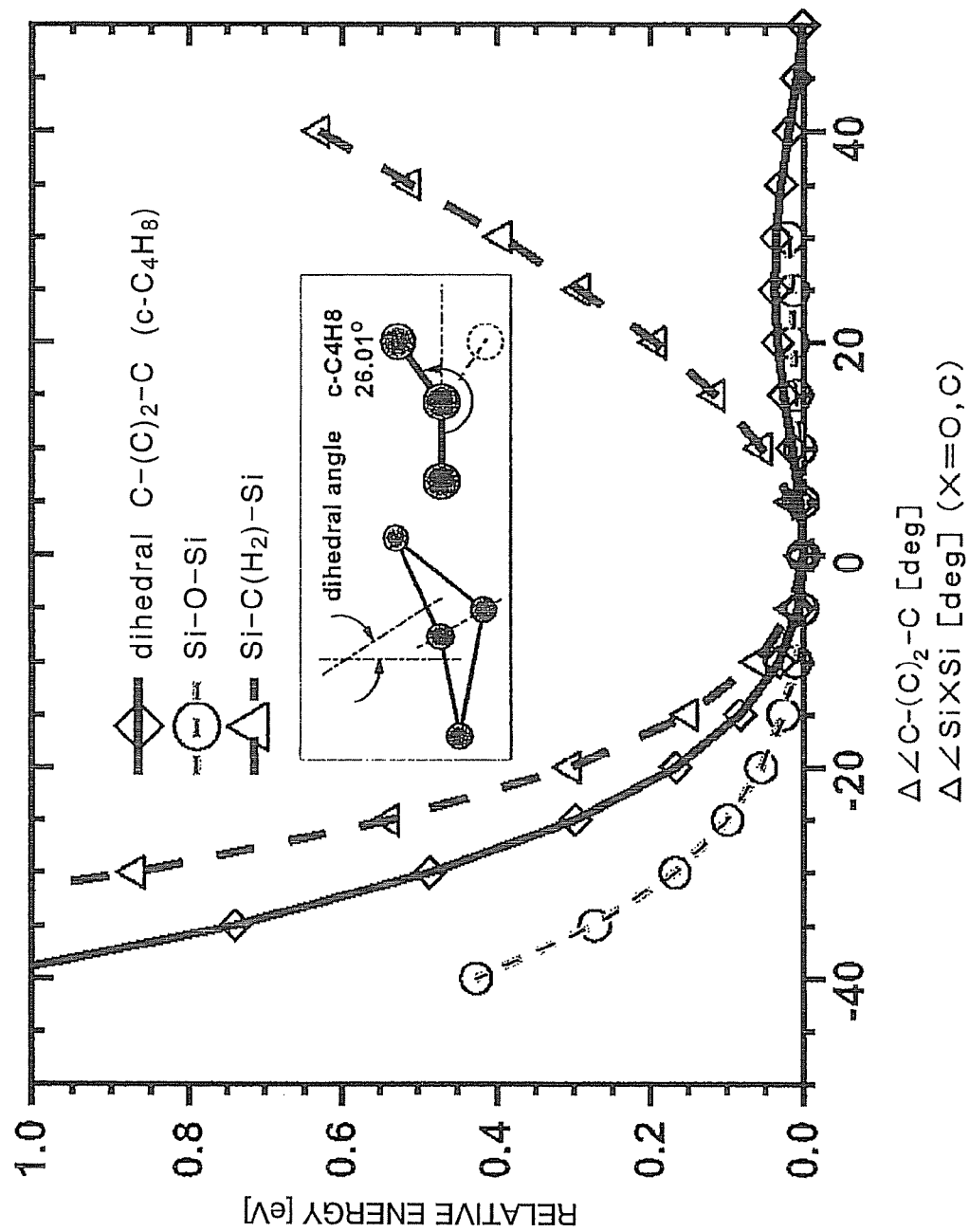
FIG. 1 is a graph showing a comparison of a change in potential energy curves for characteristic distortions between an isolated cyclobutane molecule and conventional linkage examples having a oxygen-linkage (siloxane skeleton) or a methylene-linkage.

The first embodiment will be described. The compositions for film formation in the first embodiment includes a silane compound represented by general formula (I) or a hydrolyzed-dehydrocondensation product thereof.

$$X^1{}_{3-m}R^1{}_m SiR^2 SiR^3{}_n X^2{}_{3-n} \qquad (I)$$

The term "hydrolyzed-dehydrocondensation product" refers to a dehydrocondensation product between silanol groups produced after the hydrolysis of the compositions or other compounds used along with the compositions. The dehydrocondensation products include not only products in which all the silanol groups have been dehydrocondensed but also products in which only a part of the silanol groups has been dehydrocondensed, and a mixture of products different from each other in degree of dehydrocondensation. From the viewpoints of lowering dielectric constant, moisture absorption resistance, and moisture absorption-induced stress corrosion cracking, however, the content of the residual silanol group is preferably low.

$R^1$ and $R^3$ represent a hydrogen atom or a monovalent substituent that is a non-hydrolysable group. $R^1$ and $R^3$ preferably represent a hydrogen atom, an alkyl group, or an aryl group, more preferably a hydrogen atom, a methyl group, or a phenyl group, most preferably a methyl group.

$R^2$ represents a divalent group containing an alicyclic structure with four carbon atoms or a derivative thereof. Examples of alicyclic rings include cyclobutane ($—C_4H_6—$), cyclofluorobutane ($—C_4H_{6-X}F_X—$), cyclopolymethylbutane ($—C_4H_{6-X}(CH_3)_X—$), cyclopolymethylfluorobutane ($—C_4H_{6-Y-Z}(F_Y(CH_3)_Z)—$), cyclochlorobutane ($—C_4H_{6-X}Cl_X—$), or cyclopolymethylchlorobutane ($—C_4H_{6-Y-Z}(Cl_Y(CH_3)_Z)—$). In the formulae, X is an integer of from 1 to 6, and Y and Z are an integer of from 1 to 5 and satisfy a relationship of $2 \leq Y+Z \leq 6$.

These alicyclic rings may have a substituent. In this case, examples of substituents include alkyl groups and halogen atoms such as a fluorine atom. The total number of carbon atoms per one substituent is generally 10 or less.

The divalent group containing an alicyclic structure indicated by $R^2$ should be a divalent group of the alicylic structure per se. Alternatively, not only atomic substituents but also other monovalent groups or divalent groups such as an alkylene group may be contained as substituents together with the alicyclic-linkage structure. The total number of carbon atoms in the divalent group of the alicyclic-linkage skeleton per se indicated by $R^2$ is preferably from 5 to 20, more preferably from 5 to 8. The above number of carbon atoms includes four carbon atoms constituting the basic alicyclic structure. In this case, when the alicyclic structure moiety per se is, for example, an unsaturated alicyclic ring such as cyclobutene (—$C_4H_4$—), the dihedral angle, which is inherently non-zero value in the saturated alicyclic ring, becomes substantially zero in the main skeleton (—$C_4$—) moiety although this depends upon the substituent to some extent. Therefore, the alicyclic structure moiety per se is preferably a saturated alicyclic structure rather than the unsaturated alicyclic structure.

$X^1$ and $X^2$ represent a hydrolysable group, preferably an alkoxy group, an aryloxy group, an acyloxy group, an arylcarbonyloxy group, or a halogen atom. More preferred groups are such as a methoxy group, an ethoxy group, a fluorine atom, or a chlorine atom. The fluorine atom is more preferred than the chlorine atom from the viewpoint of the dielectric constant. Halogen elements which are heavier than bromine are preferred from the viewpoint of easier synthesis. These halogen elements, however, increase polarizability and thus are excluded from the viewpoint of dielectric constant.

m and n are an integer of from 0 to 2. When m=n=0, un-dehydrocondensed silanol groups are likely to remain in the film after the formation of an insulating film. Accordingly, a requirement of m+n≦1 is preferably satisfied. m=n=1 is most preferred. The ratio of the number of cross-linking groups $R^2$ to the number of Si atom in the skeleton, i.e., $R^2$/Si, is preferably 0.5 or more and 2 or less. This is because each Si atom in the skeleton preferably bonds with a cross-linking group $R^2$ by at least one bond among four bonds per Si atom. Taking the fact into consideration that one cross-linking group links two Si atoms, and focusing on $R^2$, the silane compound can be represented by rational formula: $Si(R^2_{1/2})_x(R'_{1/2})_{4-x}$ wherein $4 \geqq x \geqq 1$.

Specific examples of silane compounds represented by general formula (I) are as follows. The present invention, however, is not limited to these compounds.

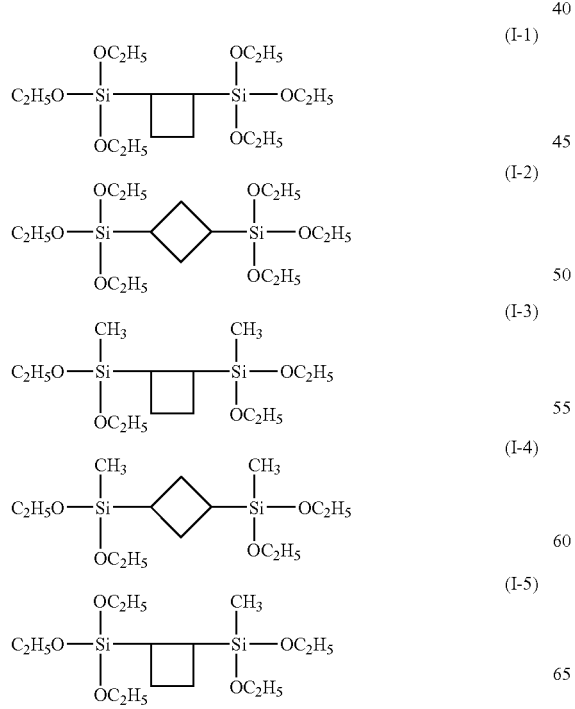

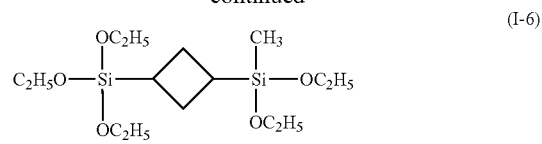

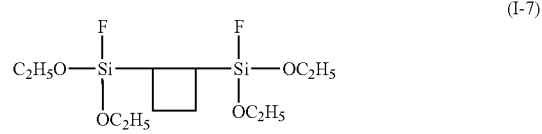

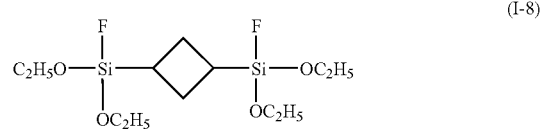

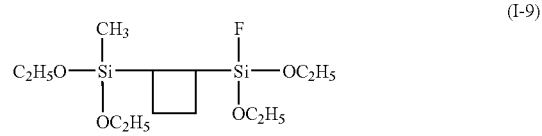

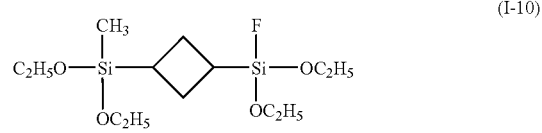

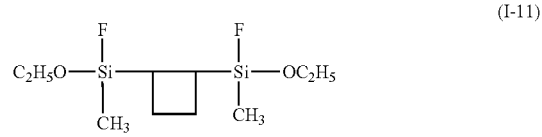

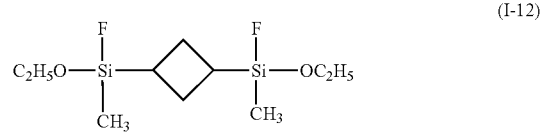

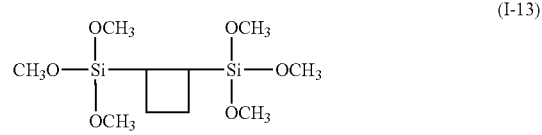

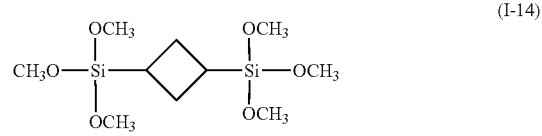

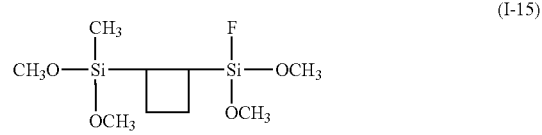

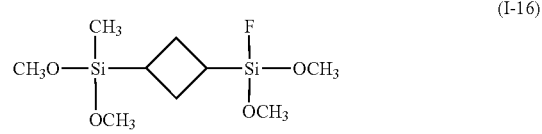

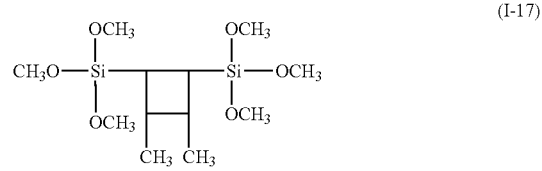

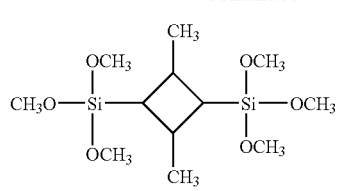
(I-18)

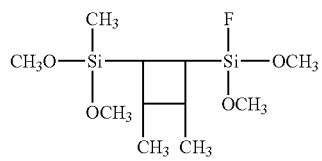
(I-19)

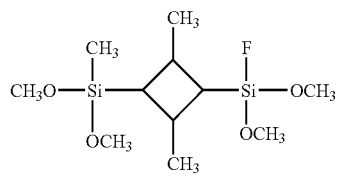
(I-20)

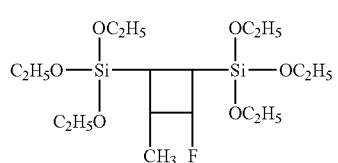
(I-21)

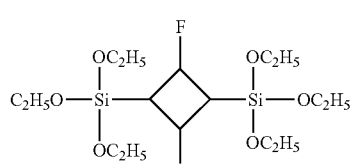
(I-22)

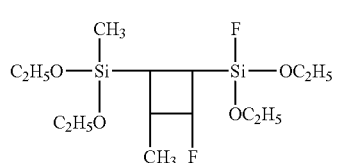
(I-23)

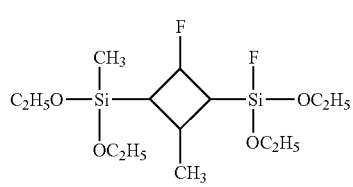
(I-24)

The compositions for film formation in this embodiment may contain a silane compound represented by general formula (II) or a hydrolyzate thereof in addition to the silane compound represented by general formula (I) or a hydrolyzate thereof.

(II)

wherein $R^4$ represents a hydrogen atom or a substituent which is a non-hydrolysable group, preferably a methyl group, a phenyl group, or a cycloalkyl group.

$X^3$ represents a hydrolysable group. Examples of $X^3$ include alkoxy groups, aryloxy groups, halogen atoms, and acyl groups. Alkoxy groups are preferred as $X^3$, for example, from the viewpoint of stability both of a coating liquid and of a precursor for CVD methods. Lower alkoxy groups with carbon atoms from 1 to 5 are preferred as the alkoxy group. The alkoxy groups may be in a normal-chain or branched form. Further, hydrogen atoms in the alkoxy group may be substituted, for example, by fluorine atoms. $X^3$ is most preferably a methoxy group or an ethoxy group. And, p is an integer of from 0 to 3 and is preferably from 0 to 2 from the viewpoint mechanical strength of the film.

Specific examples of silane compounds represented by general formula (II) include dimethyldiethoxysilane, methyltrimethoxysilane, methyltriethoxysilane, phenyltrimethoxysilane, and tetraethoxysilane.

The addition amount of the silane compound represented by general formula (II) is preferably from 1 to 1000 mol % more preferably from 5 to 500 mol %, based on the silane compound represented by general formula (I).

When the silane compound represented by general formula (I) or (II) is hydrolyzed or dehydrocondensed, the use of water in an amount of from 0.5 to 150 mols per one mol of the compound is preferred. The addition of from 1 to 100 mols, per one mol of the compound, of water is particularly preferred. When the amount of water added is less than 0.5 mol, the cracking resistance of the film is sometimes poor. On the other hand, when the amount of water added is more than 150 mols, precipitation or gelation of the polymer sometimes takes place during hydrolysis and dehydrocondensation.

The compositions for film formation in this embodiment may further contain a solvent. Solvents usable herein include ethylene dichloride, cyclohexanone, cyclopentanone, 2-heptanone, methyl isobutyl ketone, γ-butyrolactone, methyl ethyl ketone, methanol, ethanol, dimethylimidazolidinone, ethylene glycol monomethyl ether, ethylene glycol monoethyl ether, ethylene glycol dimethyl ether, 2-methoxyethyl acetate, ethylene glycol monoethyl ether acetate, propylene glycol monomethyl ether (PGME), propylene glycol monomethyl ether acetate (PGMEA), tetraethylene glycol dimethyl ether, triethylene glycol monobutyl ether, triethylene glycol monomethyl ether, isopropanol, ethylene carbonate, ethyl acetate, butyl acetate, methyl lactate, ethyl lactate, methyl methoxypropionate, ethyl ethoxypropionate, methyl pyruvate, ethyl pyruvate, propyl pyruvate, N,N-dimethylformamide, dimethylacetoamide, dimethyl sulfoxide, N-methylpyrrolidone, tetrahydrofuran, diisopropylbenzene, toluene, xylene, and mesitylene. These solvents may be used either solely or as a mixture thereof.

Among them, preferred solvents are propylene glycol monomethyl ether acetate, propylene glycol monomethyl ether, 2-heptanone, cyclohexanone, γ-butyrolactone, ethylene glycol monomethyl ether, ethylene glycol monoethyl ether, ethylene glycol monoethyl ether acetate, propylene glycol monomethyl ether, propylene glycol monoethyl ether, ethylene carbonate, butyl acetate, methyl lactate, ethyl lactate, methyl methoxypropionate, ethyl ethoxypropionate, N-methylpyrrolidone, N,N-dimethylformamide, tetrahydrofuran, methyl isobutyl ketone, xylene, mesitylene, and diisopropylbenzene.

A method for low-k insulating film formation using the compositions for film formation will be described. The term "low-k insulating film" as used herein refers to an insulating film embedded in a portion between interconnects in order to prevent so-called RC-delay (i.e. wiring delay parameter as a product of the interconnect resistance (R) and the capacity (C) between interconnects) attributable to multilayer interconnections in higher integration of ultralarge scale integrated circuits (ULSIs) and specifically refers to a film having a dielectric constant of not more than 2.6. According to this embodiment, an organosilicon oxide film having a dielectric constant of larger than 1.0 and not more than 2.6 can be formed. The dielectric constant can be further lowered, for example, by adding a heat-decomposable compound or the like to a composition for film formation to make a film more porous.

At the outset, a composition for film formation is provided. Specifically, a silane compound represented by general formula (I) and optionally a silane compound represented by general formula (II) are provided. The silane compound represented by general formula (I) may be produced by the following process.

The silane compound represented by general formula (I) can be synthesized, for example, by a hydrosilylation reaction using a cycloalkyldiene compound and a silane hydride compound or by a reaction of a Grignard reagent, synthesized from a cycloalkane dihalide, with an alkoxysilane compound.

A process, in which two allene ($H_2C=C=CH_2$) molecules, i.e., a compound having three carbon atoms linked to each other in a straight chain through double bonds are dimerized by a thermal reaction to produce dimethylenecyclobutane, has been known from long ago. This synthetic process, however, have to be carried out under severe reaction conditions and produces a mixture of various isomers as a product. Accordingly, the usefulness of the synthetic process is low. Among structures of carbocyclic rings having a small number of carbon atoms, four-membered ring structures are most difficult to be produced by the above process as well as by other processes. Also for natural products, only a few compounds called terpenes and the like exist.

Regarding this, a synthetic process has been developed in which a selective conversion reaction of a carbon skeleton, which is so-called metallacycle, is carried out in the presence of a former periodic transition metal complex (a metal chelate compound) as a catalyst. For example, Japanese Patent No. 3718709 discloses a process which can synthesize novel cyclobutane derivatives represented by general formula (III) under moderate conditions at a high yield. Specifically, Japanese Patent No. 3718709 discloses that the cyclobutane derivatives can easily be synthesized by mere stirring at or below room temperature in the presence of a former periodic transition metal complex catalyst for a very short period of time (typically from 30 min to 3 hr).

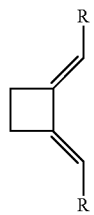

(III)

wherein Rs represent a perfluoroalkyl group having from 1 to 20 carbon atoms (for example, $C_6F_{13}$), a perfluoroaryl group having from 6 to 20 carbon atoms (for example, $C_6F_5$), CON($CH_3$)$C_6H_5$, COC$_2$H$_5$, COC$_6$H$_5$, or SO$_2$C$_6$H$_5$. The two Rs may be the same or different.

The novel cyclobutane derivatives represented by general formula (III) can be synthesized by dimerizing allene derivatives represented by general formula (IV).

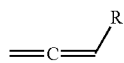

(IV)

wherein Rs represents a perfluoroalkyl group having from 1 to 20 carbon atoms (for example, $C_6F_{13}$), a perfluoroaryl group having from 6 to 20 carbon atoms (for example, $C_6F_5$), CON($CH_3$)$C_6H_5$, COC$_2$H$_5$, COC$_6$H$_5$, or SO$_2$C$_6$H$_5$.

Further, J. Org. Chem., Vol. 64, pp. 8706-8708, 1999 discloses a process in which a diarylalkyne (R—C≡C—R) is reacted with a diethyl-zirconocene catalyst and with iodine and copper(I) chloride in that order to dimerize the diarylalkyne and thus to synthesize a diarylcyclobutene represented by general formula (V). In formula (V), two Rs may be the same or different. In the stage of the completion of the conventional synthetic process, an unsaturated alicyclic ring is produced. The ring structure moiety of the unsaturated alicyclic diarylcyclobutene is a planar structure and thus does not have the effect of the present invention which will be described later. Accordingly, subsequent to the conventional synthetic process, for example, a hydrogenation reaction or a hydrogen halide addition reaction should be applied to produce a saturated alicyclic structure.

(V)

In performing hydrolysis or dehydrocondensation for producing a silane compound, which is a composition for film formation according to the present invention, represented by general formula (I) or (II), the use of a base catalyst, a metal chelate compound, or an acid catalyst is preferred.

Base catalysts include, for example, sodium hydroxide, potassium hydroxide, lithium hydroxide, pyridine, pyrrole, piperazine, pyrrolidine, piperidine, picoline, monoethanolamine, diethanolamine, dimethyl monoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, methylamine, ethylamine, propylamine, butylamine, pentylamine, hexylamine, pentylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, and 3-amino-3-methylamine. Among them, amines or amine salts are preferred, and organoamines or organoamine salts are particularly preferred. Alkylamine and tetraalkylammonium hydroxides are most preferred. Only one of these alkali catalysts may be used. Alternatively, two or more of these alkali catalysts may be simultaneously used.

Metal chelate compounds include, for example, nickel chelate compounds such as bis(cyclooctadiene).mono(triphenylphosphino)nickel, bis(triphenylphosphino).dichloronickel, bis(triphenylphosphino).dibromonickel, [1,4-bis(diphenylphosphino)butane].dichloronickel, [1,4-bis(diphenylphosphino)butane].dibromonickel, [1,2-bis(diphenylphosphino)ethane].dichloronickel, and [1,2-bis(diphenylphosphino)ethane].dibromonickel; titanium chelate compounds such as tri-ethoxy.mono(acetylacetonato)titanium, tri-n-propoxy.mono(acetylacetonato)titanium, tri-i-propoxy.mono(acetylacetonato)titanium, tri-n-butoxy.mono(acetylacetonato)titanium, tri-sec-butoxy.mono(acetylacetonato)titanium, tri-t-butoxy.mono(acetylacetonato)titanium, di-ethoxy.bis(acetylacetonato)

titanium, di-n-propoxy.bis(acetylacetonato)titanium, di-i-propoxy.bis(acetylacetonato)titanium, di-n-butoxy.bis(acetylacetonato)titanium, di-sec-butoxy.bis(acetylacetonato)titanium, di-t-butoxy.bis(acetylacetonato)titanium, mono-ethoxy.tris(acetylacetonato)titanium, mono-n-propoxy.tris(acetylacetonato)titanium, mono-i-propoxy.tris(acetylacetonato)titanium, mono-n-butoxy.tris(acetylacetonato)titanium, mono-sec-butoxy.tris(acetylacetonato)titanium, mono-t-butoxy.tris(acetylacetonato)titanium, tetrakis(acetylacetonato)titanium, tri-ethoxy.mono(ethylacetoacetate)titanium, tri-n-propoxy.mono(ethylacetoacetate)titanium, tri-i-propoxy.mono(ethylacetoacetate)titanium, tri-n-butoxy.mono(ethylacetoacetate)titanium, tri-sec-butoxy.mono(ethylacetoacetate)titanium, tri-t-butoxy.mono(ethylacetoacetate)titanium, di-ethoxy.bis(ethylacetoacetate)titanium, di-n-propoxy.bis(ethylacetoacetate)titanium, di-i-propoxy.bis(ethylacetoacetate)titanium, di-n-butoxy.bis(ethylacetoacetate)titanium, di-sec-butoxy.bis(ethylacetoacetate)titanium, di-t-butoxy.bis(ethylacetoacetate)titanium, mono-ethoxy.tris(ethylacetoacetate)titanium, mono-n-propoxy.tris(ethylacetoacetate)titanium, mono-i-propoxy.tris(ethylacetoacetate)titanium, mono-n-butoxy.tris(ethylacetoacetate)titanium, mono-sec-butoxy.tris(ethylacetoacetate)titanium, mono-t-butoxy.tris(ethylacetoacetate)titanium, tetrakis(ethylacetoacetate)titanium, mono(acetylacetonato)tris(ethylacetoacetate)titanium, bis(acetylacetonato)bis(ethylacetoacetate)titanium, and tris(acetylacetonate)mono(ethylacetoacetate)titanium; zirconium chelate compounds such as tri-ethoxy.mono(acetylacetonato)zirconium, tri-n-propoxy.mono(acetylacetonato)zirconium, tri-i-propoxy.mono(acetylacetonato)zirconium, tri-n-butoxy.mono(acetylacetonato)zirconium, tri-sec-butoxy.mono(acetylacetonato)zirconium, tri-t-butoxy.mono(acetylacetonato)zirconium, di-ethoxy.bis(acetylacetonato)zirconium, di-n-propoxy.bis(acetylacetonato)zirconium, di-i-propoxy.bis(acetylacetonato)zirconium, di-n-butoxy.bis(acetylacetonato)zirconium, di-sec-butoxy.bis(acetylacetonato)zirconium, di-t-butoxy.bis(acetylacetonato)zirconium, mono-ethoxy.tris(acetylacetonato)zirconium, mono-n-propoxy.tris(acetylacetonato)zirconium, mono-i-propoxy.tris(acetylacetonato)zirconium, mono-n-butoxy.tris(acetylacetonato)zirconium, mono-sec-butoxy.tris(acetylacetonato)zirconium, mono-t-butoxy.tris(acetylacetonato)zirconium, tetrakis(acetylacetonato)zirconium, tri-ethoxy.mono(ethylacetoacetate)zirconium, tri-n-propoxy.mono(ethylacetoacetate)zirconium, tri-i-propoxy.mono(ethylacetoacetate)zirconium, tri-n-butoxy.mono(ethylacetoacetate)zirconium, tri-sec-butoxy.mono(ethylacetoacetate)zirconium, tri-t-butoxy.mono(ethylacetoacetate)zirconium, di-ethoxy.bis(ethylacetoacetate)zirconium, di-n-propoxy.bis(ethylacetoacetate)zirconium, di-i-propoxy.bis(ethylacetoacetate)zirconium, di-n-butoxy.bis(ethylacetoacetate)zirconium, di-sec-butoxy.bis(ethylacetoacetate)zirconium, di-t-butoxy.bis(ethylacetoacetate)zirconium, mono-ethoxy.tris(ethylacetoacetate)zirconium, mono-n-propoxy.tris(ethylacetoacetate)zirconium, mono-i-propoxy.tris(ethylacetoacetate)zirconium, mono-n-butoxy.tris(ethylacetoacetate)zirconium, mono-sec-butoxy.tris(ethylacetoacetate)zirconium, mono-t-butoxy.tris(ethylacetoacetate)zirconium, tetrakis(ethylacetoacetate)zirconium, mono(acetylacetonato)tris(ethylacetoacetate)zirconium, bis(acetylacetonato)bis(ethylacetoacetate)zirconium, and tris(acetylacetonato)mono(ethylacetoacetate)zirconium; and aluminum chelate compounds such as tris(acetylacetonato)aluminum, tris(ethylacetoacetate)aluminum. Preferred are nickel complex catalysts, titanium complex catalysts, and zirconium complex catalysts that are former periodic transition metal complexes (metal chelate compounds). More preferred are zirconium complex catalysts such as the so-called zirconocene diethyl. Only one of these metal chelate compounds may be used. Alternatively, two or more of these metal chelate compounds may be simultaneously used.

Acid catalysts include, for example, inorganic acids such as hydrochloric acid, nitric acid, sulfuric acid, hydrofluoric acid, phosphoric acid, boric acid, and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolyzate of glutaric acid, a hydrolyzate of maleic anhydride, and a hydrolyzate of phthalic anhydride. Organocarboxylic acids are more preferred. Only one of these acid catalysts may be used. Alternatively, two or more of these acid catalysts may be simultaneously used.

The amount of the catalyst used is generally from 0.00001 to 10 mols, preferably from 0.00005 to 5 mols, per one mol of the silane compound such as compounds represented by general formula (I) or (II). When the amount of the catalyst used falls within the above specified range, the precipitation or gelation of polymer during the reaction is less likely to occur. In the present invention, the hydrolysis and dehydrocondensation of the silane compound are carried out generally at from 0 to 100° C., preferably from 10 to 90° C., generally for from 5 min to 40 hr, preferably from 10 min to 20 hr from the viewpoint of process throughput.

Separately from the above mentioned synthetic process using a conversion reaction of a carbon skeleton in the presence of a former periodic transition metal complex catalyst called metallacycle, JP-A 2007-119488 (KOKAI) discloses that a polysubstituted cyclobutane compound or a polysubstituted cyclobutene compound can be synthesized in an efficient, stereoselective and ecological manner by allowing Broensted acid to act on an enol ether compound or a 2-siloxydiene compound and an alkene compound having a carbonyl group as a substituent at the 1-position or an alkyne compound having a carbonyl group as a substituent at the 1-position in the absence of a solvent or in a non-aqueous solvent.

Synthesis of a polysubstituted cyclobutane compound will be described as an example. A polysubstituted cyclobutane compound represented by general formula (VIII) can be synthesized by reacting an enol ether compound represented by general formula (VI) with an alkene compound represented by general formula (VII) in the presence of a Broensted acid catalyst in a non-aqueous solvent.

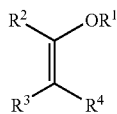
(VI)

wherein $R^1$ represents an optionally substituted alkyl group, an optionally substituted aryl group, an optionally substituted heterocyclic group, or an optionally substituted silyl group; and $R^2$, $R^3$ and $R^4$, which may be the same or different, each independently represent a hydrogen atom, a halogen atom, an optionally substituted alkyl group, an optionally substituted aryl group, an optionally substituted heterocyclic group, an optionally substituted silyl group, or an optionally substituted alkylalkoxy group. The substituents $R^1$ to $R^4$ may be bonded to each other.

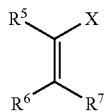
(VII)

wherein X represents an ester carbonyl group, an amide carbonyl group, a ketocarbonyl group, an aldehyde group, a perfluoroalkyl group (for example, $C_6F_{13}$), a perfluoroaryl group (for example, $C_6F_5$), $CON(CH_3)C_6H_5$, $COC_2H_5$, $COC_6H_5$, or $SO_2C_6H_5$; and $R^5$, $R^6$ and $R^7$, which may be the same or different, each independently represent a hydrogen atom, a halogen atom, an optionally substituted alkyl group, an optionally substituted aryl group, an optionally substituted silyl group, or an optionally substituted heterocyclic group. The substituents X and $R^5$ to $R^7$ may be bonded to each other.

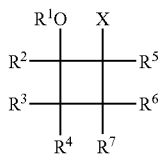
(VIII)

wherein the substitutents X and $R^1$ to $R^7$ are as defined in general formulae (VI) and (VII).

Stereo-isomers represented by general formula (IX), in which a substituent X and an oxygen substituent on the four-membered ring are in a trans relationship, can be selectively synthesized by the above production process.

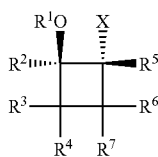
(IX)

wherein substituents X and $R^1$ to $R^7$ are as defined in general formulae (VI) and (VII). In this case, the substituent X in the alkene compound as the starting compound is preferably an ester carbonyl group, and examples thereof include an alkoxy carbonyl group and a polyhaloalkoxy carbonyl group. The enol ether compound as the starting compound is preferably a silyl enol ether, and examples thereof include enol ethers substituted by a triisopropylsilyl group or a tert-butyldimethylsilyl group.

In this embodiment, preferably, among $R^1$ to $R^7$, the substituents bonded to two different carbon atoms in the four-membered ring are chosen among a silyl group, and X is chosen among a perfluoroalkyl group (for example, $C_6F_{13}$), a perfluoroaryl group (for example, $C_6F_5$), $CON(CH_3)C_6H_5$, $COC_2H_5$, $COC_6H_5$, or $SO_2C_6H_5$.

Preferred Broensted acids are strong acids such as trifluoromethanesulfonic acid imides, pentafluorobenzenesulfonic acid imides, bis(pentafluoroethyl)phosphoric acid, or substituted polyfluoroalkylsulfonic acid groups represented by general formula (X).

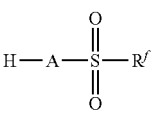
(X)

wherein A represents a nitrogen, oxygen, carbon, sulfur, or phosphorus atom that is, chemically-allowed, either un-substituted or plurally substituted atom; and $R^f$ represents an alkyl, aryl or heterocyclic group substituted by two or more fluorine atoms.

Specific examples of Broensted acids include bis(trifluoromethanesulfonic acid)imide, bis(pentafluoroethanesulfonic acid)imide, bis(pentafluorobenzenesulfonic acid) imide, N-pentafluorobenzenesulfonyl-N-trifluoromethanesulfonic acid imide, N-trifluoromethanesulfonyl-N-trifluoromethanesulfonic acid imide, trifluoromethanesulfonic acid, pentafluoroethane sulfonic acid, tris(trifluoromethanesulfonyl)methane, tris(pentafluorobenzenesulfonyl)methane, and bis(pentafluorobenzenesulfonyl)tolufluoromethanesulfonylmethane.

Also in this embodiment, a composition for film formation, in which portions between Si atoms have been cross-linked by a divalent group containing an alicyclic structure with four carbon atoms or a derivative thereof, can be synthesized by properly applying the above synthetic processes and using a Si-containing functional group as R bonded to the alicyclic structure with four carbon atoms.

The total solid content of the compositions for film formation is preferably from 2 to 30 wt % and is properly regulated depending upon methods by which a film is formed using the compositions for film formation, for example, film formation by coating (such as spin coating) or film formation by chemical vapor deposition (CVD). The reason why the total solid content of the compositions for film formation is from 2 to 30 wt % is as follows. When a film is formed by coating the compositions for film formation on a substrate such as a silicon wafer, an $SiO_2$ layer on the wafer, or an SiN layer on the wafer, the thickness of the formed coating film becomes within a suitable thickness range and, further, better stability for storage of the coating liquid can be realized. A film may also be formed by supplying the gases containing compositions for film formation together with non-oxidizing diluting gases or oxidizing gases onto a substrate and depositing them as a low-k insulating film onto the substrate, for example, by thermal CVD or plasma CVD. Also in this case, the compositions for film formation can be provided as a liquid source by diluting the compositions for film formation with the above solvent for dilution stabilization. Accordingly, the compositions for film formation can be supplied as a starting gas for CVD, for example, through evaporation by heating or bubbling evaporation using a carrier gas.

Thus, after the composition for film formation according to the present invention synthesized by the above disclosed synthetic processes is provided, a low-k insulating film can be formed, for example, by a coating method or a CVD method.

Coating Method

In forming a film by a coating method, the composition for film formation is first diluted with the above solvent and the diluted solution is coated onto a substrate such as a silicon wafer. Examples of coating means include spin coating, dipping, roll coating, and spraying. In this case, a film having a thickness of about from 0.05 to 1.5 mm on a dry solid basis can be formed by single coating, and a film having a thickness of about from 0.1 to 3 mm on a dry solid basis can be formed by double coating. Thereafter, the residual solvent is removed by volatizing it at room temperature or by heating using a hot plate, an oven, a furnace or the like to allow the removal of the residual solvent and cross-linking reactions to proceed, whereby a film with vitreous characteristics or a film like macromolecules or a film of a mixture having both characteristics can be formed.

The heating may be carried out, for example, in a nitrogen atmosphere or an argon atmosphere, or under vacuum. Preferably, the heating is carried out under such conditions that the maximum value of the heating temperature is 200° C. or above and 600° C. or below. Particularly preferably, from the viewpoints of suppressing both stress and crack generation caused by shrinkage of the insulating film, the heating is carried out under such conditions that the maximum value of the heating temperature is 300° C. or above and 430° C. or below. The heating period is generally from 1 min to 20 hr, preferably from 15 min to 10 hr from the viewpoint of process throughput.

This film may be treated, for example, by additional annealing, ultraviolet photon irradiation, or electron beam irradiation. In the ultraviolet photon irradiation and electron beam irradiation, both direct excitation and breakage of unnecessary bonds in the cross-linkage structure followed by bond formation by the energy beam are not always necessary. A method may be adopted in which reactive oxygen, for example, dissolved oxygen, OH group or the like in its excited states, an oxygen atom produced by exciting a solvent, dissolved oxygen, OH group or the like, or an oxygen atom produced by a reaction of the excited species, for example, with a dissolved hydrogen atom or the like is used to oxidize and break unnecessary bonds in the cross-linkage structure and to perform bond formation, whereby a desired cross-linkage structure is formed.

Specifically, a low-k insulating film with high mechanical-strength can be formed by coating the compositions for film formation onto a substrate (generally a substrate having a metallic interconnect), for example, by spin coating, and previously heating the coating to volatize and remove the residual solvent and to cross-link the siloxane group contained in the compositions for film formation to some extent and then heating (annealing) the dried coated films at a temperature of 300° C. or above and 430° C. or below to complete the cross-linking reaction.

CVD Method

In forming a film by a CVD method, a liquid source is provided by first diluting the compositions for film formation with the above solvent to stabilize the compositions for film formation. A desired low-k insulating film of a vitreous characteristics or a film like macromolecules or a mixture having both characteristics can be formed by supplying the liquid source as a CVD source gas, for example, through evaporation by heating or bubbling evaporation using a carrier gas, together with other non-oxidizing diluting gases or oxidizing gases onto a substrate to deposit the compositions for film formation.

Additional heating, ultraviolet photon irradiation, electron beam irradiation or the like to optimize the degree of progress of the cross-linking reaction can convert a vitreous deposit, a deposit like macromolecules or a mixture having both characteristics into a desired film. The resultant film can constitute an insulator having low-k, high mechanical-strength, low moisture absorption, and high plasma treatment resistance. Regarding the ultraviolet photon irradiation and electron beam irradiation, both direct excitation and breakage of unnecessary bonds in the cross-linkage structure followed by bond formation by the energy beam are not always necessary. A method may be adopted in which reactive oxygen, for example, dissolved oxygen, OH group or the like in its excited states, an oxygen atom produced by exciting a solvent, dissolved oxygen, OH group or the like, or an oxygen atom produced by a reaction of the excited species, for example, with a dissolved hydrogen atom or the like is used to oxidize and break unnecessary bonds in the cross-linkage structure and to perform bond formation, whereby a desired cross-linkage structure is formed.

The treatment may be carried out, for example, in a nitrogen atmosphere or an argon atmosphere, or under vacuum. Preferably, the heating is carried out under such conditions that the maximum value of the heating temperature is 200° C. or above and 600° C. or below. Particularly preferably, from the viewpoints of suppressing both stress and crack generation by shrinkage of the insulating film, the heating is carried out under such conditions that the maximum value of the heating temperature is 300° C. or above and 430° C. or below. The heating time is generally from 1 min to 20 hr. As with the formation of the film by coating, the heating period is preferably from 15 min to 10 hr from the viewpoint of process throughput.

The low-k insulating film thus obtained by coating methods or CVD methods is excellent in insulating properties and dielectric properties, as well as in moisture absorption resistance, cracking resistance, evenness of the thickness and quality of the film, and surface hardness. Accordingly, the low-k insulating film is useful as interlayer insulating films for semiconductor devices, for example, LSIs, system LSIs, DRAMs, SDRAMs, RDRAMs, and D-RDRAMs and further is useful for other applications such as protective films such as surface coating films for semiconductor devices, interlayer insulating films for multilayer interconnect boards, and protective films and insulating films for liquid crystal display elements. In the interlayer insulating film for semiconductor devices, the application to a site where generation of a large tensile stress has been unavoidable is particularly suitable.

The principles of the present invention is very important to distinguish the present invention from cross-linking by a hydrocarbon group R (for example, a polymethylene group or a phenylene group) by conventional techniques and thus will be described in more detail.

Conventional techniques mainly aim at an improvement in hardness of Si—R—Si skeleton for mechanical strength improvement purposes (enhancing mechanical-strengths for a tensile deformation in a main chain direction, for a bending deformation in a direction perpendicular to the main chain, or for a torsional deformation around the main chain). The guiding principles in order to attain the purpose is to increase the number of carbon atoms in Si—$(C)_n$—Si cross-linkages or to utilize a planar structure of the benzene ring as cross-linkages, because the Si—C—Si cross-linkage is stiffer than the Si—O—Si cross-linkage. Cross-linkage by carbon (C) is likely to be fixed against bending in a direction perpendicular to the main chain or torsion around the main chain because of the nature of either $sp^3$- or $sp^2$-hybrid orbitals of C.

On the other hand, in the oxygen (O) cross-linkage, the Si—O bond per se is also strong. Since, however, the O atom ordinarily has twofold coordination, the degree of freedom of rotation or torsional deformation around O is so high enough that the O cross-linkages appears to be "flexible" ones. The flexibility permits escape of stress in the repetition of rapid application/release of mechanical stresses, for example, in a CMP process. When the hardness is merely high, the film cannot withstand a change in both stress strength and stress direction and leads to breakage of the film. On the other hand, a film with a proper level of flexibility can allow the stresses to escape. As has been reported already, a long hydrocarbon group cross-linkage moiety is suitable for achieving the flexibility.

However, when the proportion of the hydrocarbon cross-linkage structure is increased by using relatively large (or long) cross-linkage groups such as a polymethylene group or a phenylene group, cross-linkage-free gaps (pores) are disadvantageously increased. The increment in the gaps results in increasing moisture absorption and deteriorating moisture absorption resistance. Moisture absorption induces stress corrosion cracking at sites to which a large tensile stress tends to be applied, resulting in breakage of the film. That is, satisfying three requirements, i.e., hardness, flexibility, and suppression of gap formation, is important for selecting the cross-linkage structures. A cross-linkage structure of a divalent group containing an alicyclic-linkage skeleton having four carbon atoms in the skeleton per se or a derivative thereof is optimal as a cross-linkage structure satisfying the three requirements. This will be described below.

Figure 3:
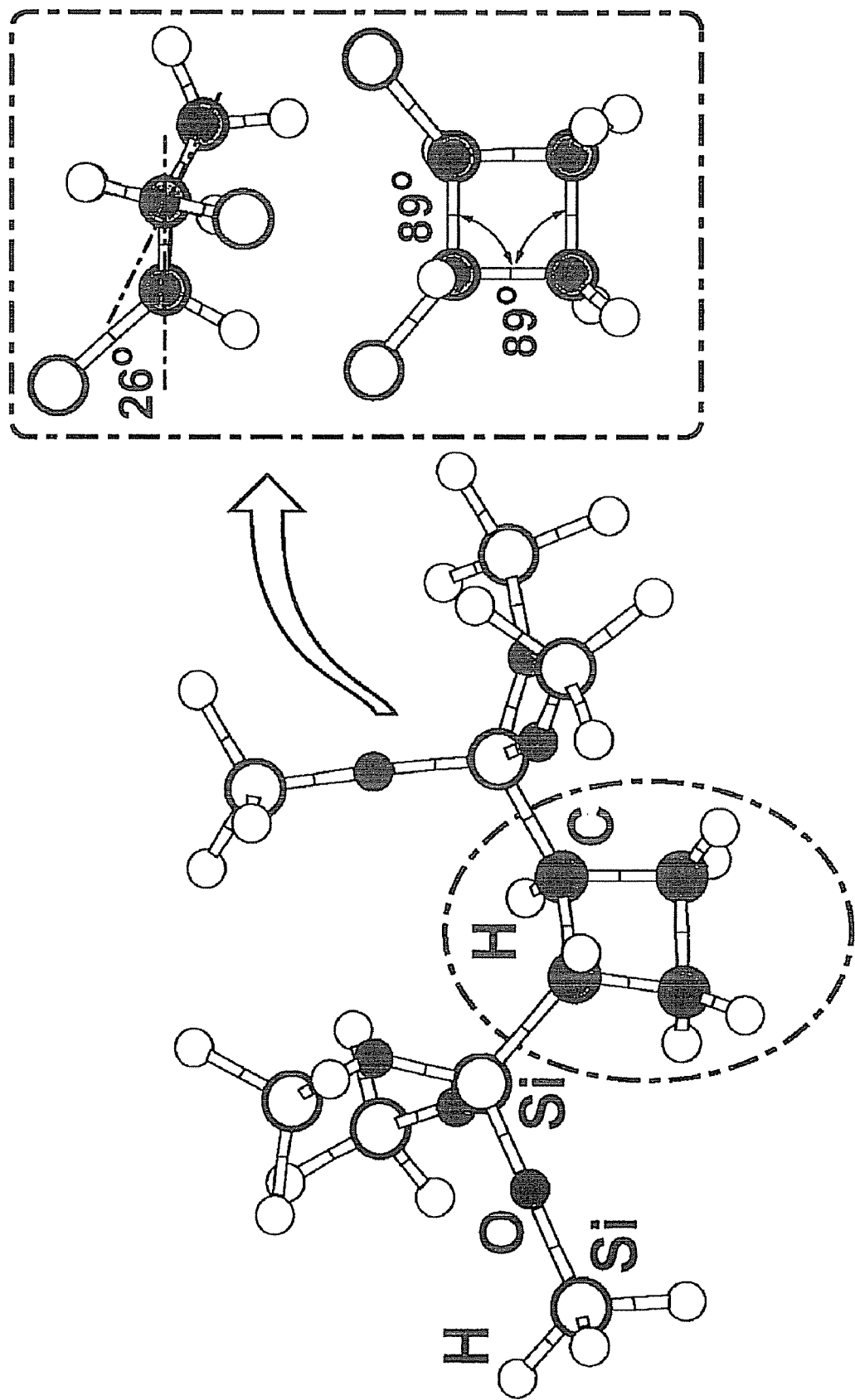
FIG. 3 is a molecular model for the ortho-position cross-linkage of trans-isomers in a cyclobutane cross-linked organosilicon oxide film.
Figure 7:
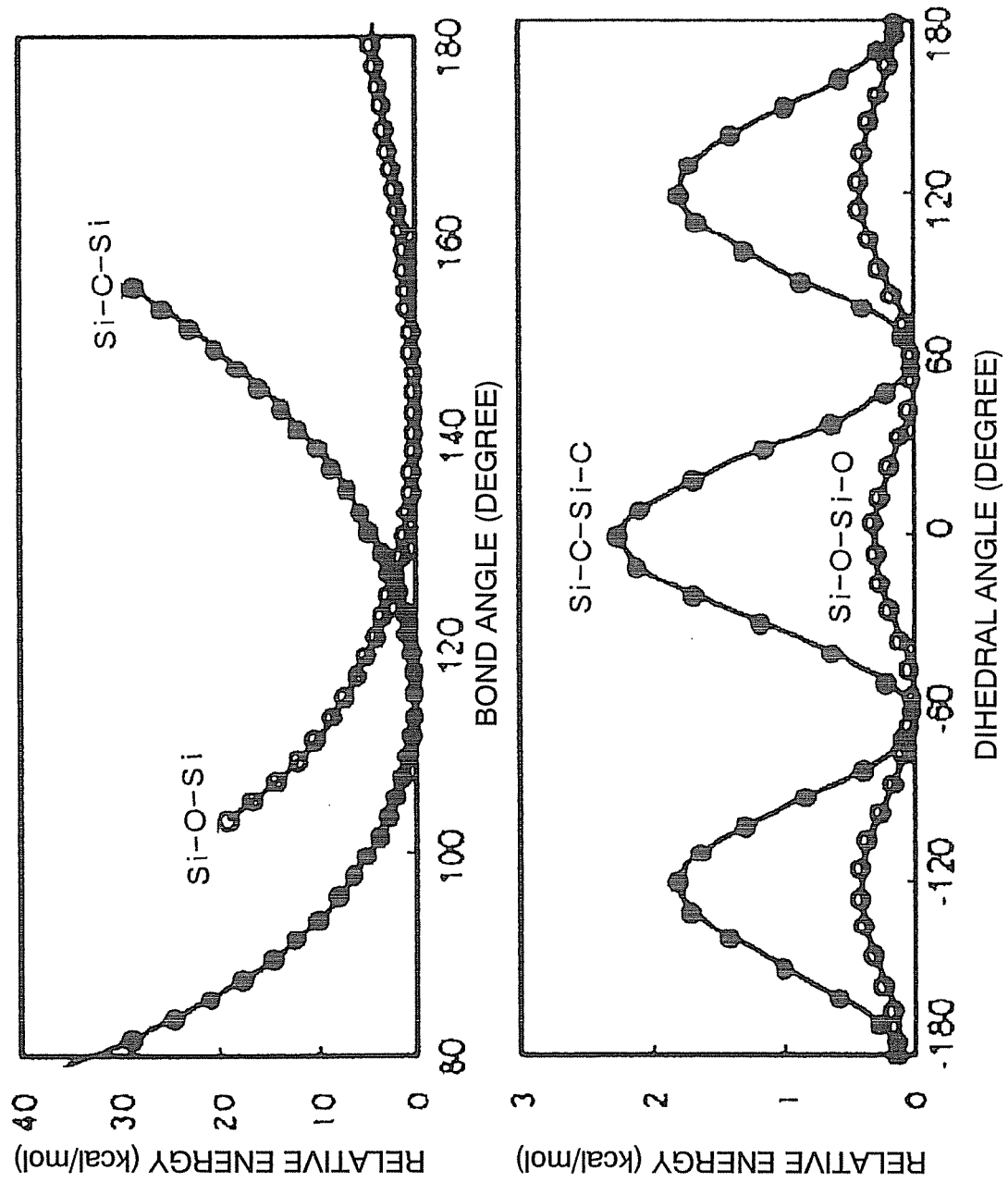
FIGS. 7A and 7B are graphs showing a change in potential energy curves as a function of a change in both bond angle and dihedral angle in an oxygen-linkage (siloxane skeleton) and a methylene-linkage as conventional examples.

FIGS. 7A and 7B are graphs showing calculated values of a change in potential energy as a function of an external distortion in the case of a monomethylene (—CH$_2$—) cross-linkage between Si atoms and an oxygen cross-linkage (siloxane skeleton) between Si atoms as disclosed in FIG. 3 in the above reference 1. A bond angle of Si—X—Si or a dihedral angle (torsional angle) of Si—X—Si—X in the cross-linkage moiety is adopted as the external distortion. Here X=C or O atoms. The vertical axis represents the change in total energies of model molecules used in the quantum chemical calculation. The graph shows that, under an identical external distortion, the internal energies increase (corresponds for the model molecules to become unstable) with increasing the curvature (sharpness) of the curves. That is, this corresponds to a "stiff or hard" structure. The drawing shows that the monomethylene cross-linkage is stiffer than the oxygen cross-linkage against both deformation of the bond angle and dihedral angle. In particular, the methylene cross-linkage is particularly stiff against such deformation of the bond angle where the oxygen cross-linkage is relatively easy to be increased its bond angle to about 180°. The graph shows that, for the oxygen cross-linkage, due to the high degree of freedom in deformation around oxygen, the Si—O—Si bond which has an bond angle around 144° in its equilibrium structure can be deformed so as to be bent in a reverse direction and, consequently, a potential energy exhibits very moderate change on a wide-angle region. On the contrary, such deformation is much less likely to occur in Si—C—Si cross-linkage. Further, the graph shows that the amount of a change in potential energies (accumulation of distortion energies) against a change in dihedral angle (torsional angle) is one order of magnitude smaller than that against a change in the bond angle. This implies that the influence of the difference is small in actual deformation in dihedral angle. Both reference 1 and reference 2 related to the reference 1 investigate an optimal cross-linkage structure aiming at search for only the hardness mentioned here.

However, the guiding principles of the optimal cross-linkage structure in the present invention has been elucidated for the first time by detailed examination of the mechanisms for the difference using ab-initio molecular orbital calculations. The guiding principles will be described with reference to FIGS. 2 to 13. The total energy calculations were carried out within an ab-initio molecular orbital theory according to a procedure consisting of preparing a model molecule containing a cross-linkage structure to be examined, optimizing the structure under the constraint of applied external distortion which should be taken into consideration. All calculations were performed at the B3LYP/6-31G (d', p') level of theory. A model molecule, in which an outer Si oxide film portion connected to a cross-linkage moiety (Si—R—Si) to be focused is terminated by three —O—SiH$_3$ groups for each Si in the moiety, has been adopted for simplification except for bond energy calculation unless otherwise specified. For the bond energy calculation, since the effect of the second nearest neighbor atom around the breakage site is negligible, model molecules with various terminations have been used.

Figure 8:
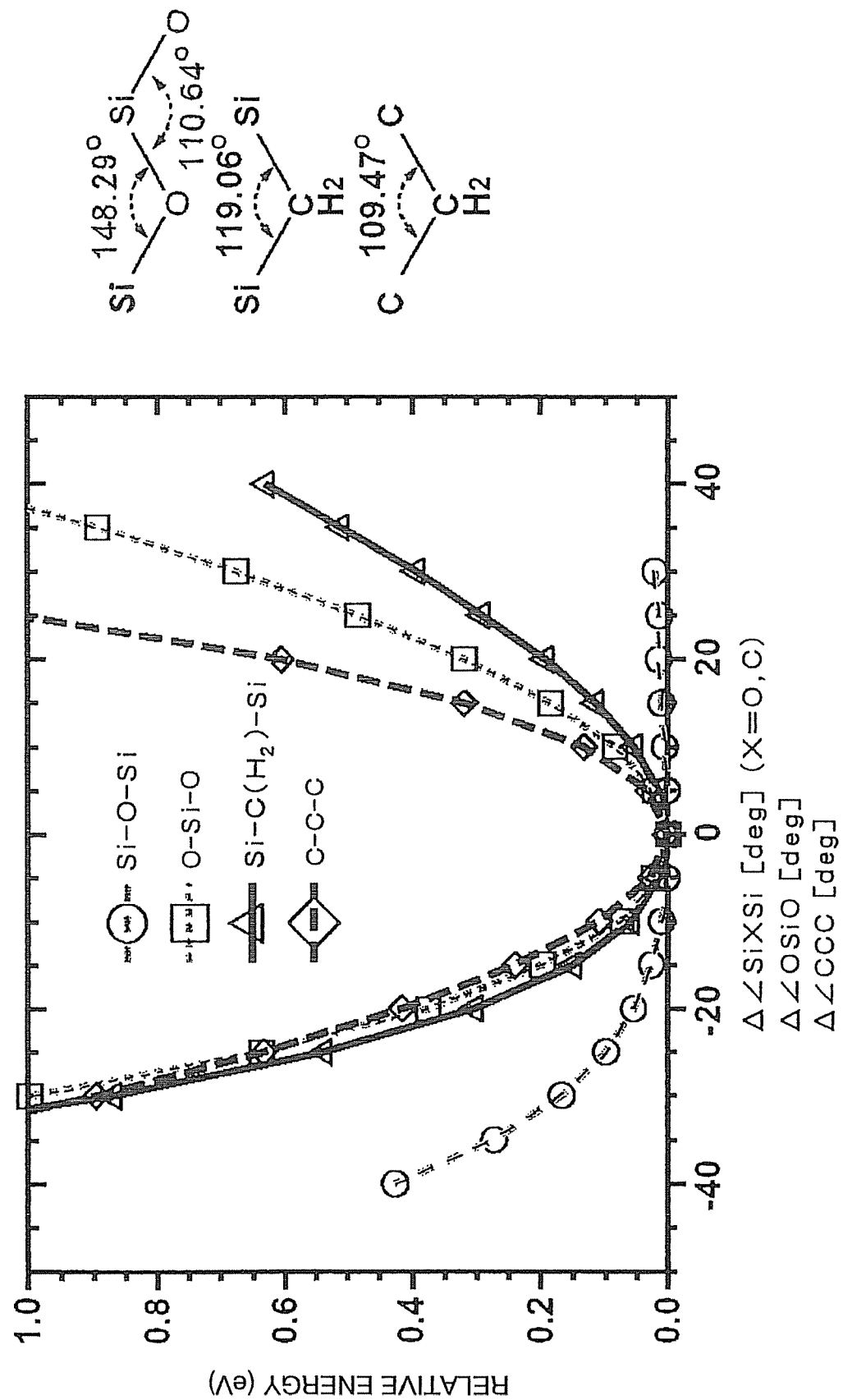
FIG. 8 is a graph showing a change in potential energy curves for characteristic distortions in various types of cross-linkages along with a linkage in diamond as conventional examples.

FIG. 8 is a graph showing a change in potential energy curves for characteristic distortions in various types of cross-linkages along with a linkage in diamond as conventional examples corresponding to FIG. 7A. Regarding the results for Si—O—Si and Si—C—Si, FIG. 8 is the same as FIG. 7A, except that the bond angle on the abscissa is translated into a relative change in the bond angle from its most stable structure. The bond angles in the most stable structures are shown on the right side of the graph for each cross-linkage cases. A change in bond angle around Si (O—Si—O) is also shown in FIG. 8. When a single bond is formed, both Si and C take an $sp^3$ hybridization. Accordingly, it is expected that Si—C—Si and O—Si—O exhibit the same tendency. This is also supported by the results shown here. The results show that the hardness of O—Si—O is equal to or somewhat larger than the hardness of Si—C—Si. Considering only the above results, however, it is difficult for fully understanding the reason why the Young's modulus of the conventional organosilicon oxide film is so low as less than 10 GPa, although the modulus of the CVD silicon oxide film is as large as 70 GPa.

Figure 10:
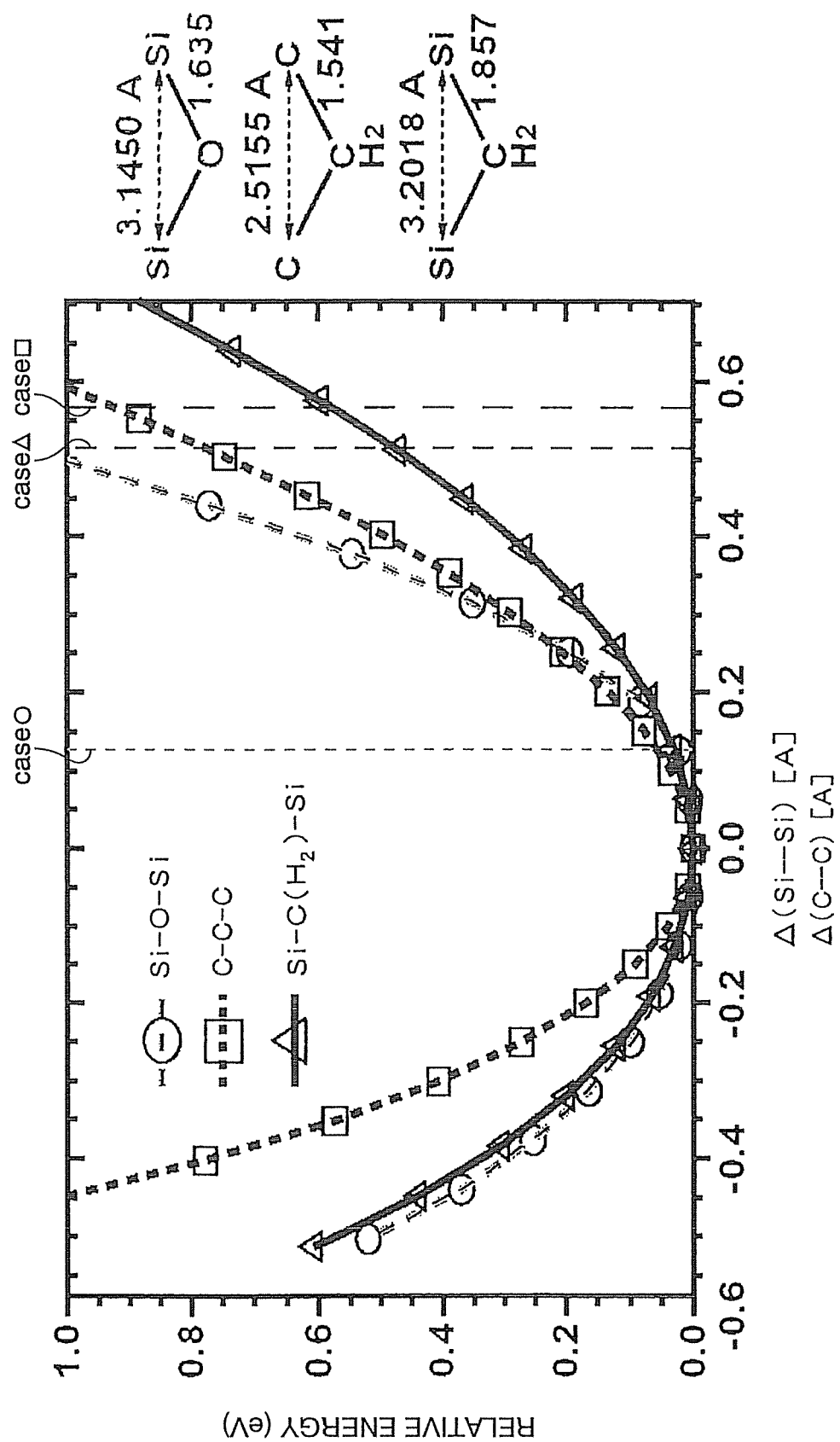
FIG. 10 is a graph showing a change in potential energy curves for stretching distortions (changes in Si . . . Si distance or C . . . C distance) in various types of cross-linkages as conventional examples.

The above phenomenon can be fully understood by referring to FIG. 10 and Table 1. FIG. 10 is a graph showing a change in potential energy curves for stretching distortions (changes in Si . . . Si distance or C . . . C distance) in various types of cross-linkages as conventional examples under the external force in a direction that causes a change in bond length, rather than external force in a bending direction that causes a change in bond angle. In FIG. 10, dotted lines provided perpendicular to the abscissa show critical values for changes in the X . . . X distances (equal to 2r-d where r and d will be defined later). The critical values correspond to the values when the X . . . X (X=Si or C) distance (d) indicated by an arrow in each cross-linkage structure shown in the right side of the drawing is stretched until the bond angle is fully extended up to 180° under the assumption that the Si—O bond length or the C—C bond length (r) remains unchanged.

As shown in FIG. 10, for oxygen cross-linking linkage (Si—O—Si), a clear inflection point is present exists around the critical value 0.125 Å. Stretching beyond the critical level value requires a rapid increase in internal potential energy, that is, the hardness is increased. On the other hand, for carbon cross-linkage, a significant inflection point does not appear both in Si—C—Si and C—C—C. The reason for this has been elucidated by investigating the bond angles of the cross-linkage moiety in each X . . . X. Specifically, for the oxygen cross-linkage, as shown in FIG. 8, since the Si—O—Si bond angle is easily extended to 180° as shown in FIG. 8, after the angle has reached 180°, the Si—O bond per se is compelled to be stretched after the angle has reached 180°. That is, in fact, in the stretching of the X . . . X distance, while its change is small, the potential energy change occurs according to an elastic deformation potential energy plane for the bond angle change. By contrast, while its change becomes large, the switching of reliance from the elastic deformation potential energy plane for the bond angle to the elastic deformation potential energy plane for the bond length takes place and the potential energy change occurs according to the elastic deformation potential energy plane for the bond length.

On the other hand, in the carbon cross-linkage, as shown in FIG. 10, bond angle deformation of the $sp^3$ hybrid orbital of a C atom is not easy. Accordingly, even when the X . . . X (X=C or Si) distance is stretched to an apparent critical point, the bond angle of the cross-linkage moiety is still far from 180°, and is as small as from about 130° (for C—C—C) to 150° (for Si—C—Si). Therefore, even beyond the apparent critical point, the potential energy change still occurs according to the elastic potential energy plane for the bond angle deformation.

It is apparent from Table 1 that, for the oxygen cross-linkage (Si—O—Si), switching of the relevant elastic deformation potential energy planes from those for the Si—O—Si bond angle change to those for the Si—O bond length change causes a rapid increase in hardness. Table 1 shows the results of calculated dissociation enthalpy of Si—O bond and Si—C bond (that is, bond energies of single bonds thereof) for various model molecules. These results were obtained by ab-initio molecular orbital calculations at the G2 level of theory which is well-known to be very accurate (error: about 1 kcal/mol).

TABLE 1

| Bond to be focused | Model molecule | Dissociation enthalpy [eV] |
|---|---|---|
| HO—Si≡ | HO—SiH$_3$ | 5.35$_2$ (5.41) |
|  | HO—Si(SiH$_3$)$_3$ | 4.83$_2$ |
|  | HO—Si(OH)$_3$ | 6.09$_4$ |
|  | HO—Si(OSiH$_3$)$_3$ | 6.09$_3$ |
| ≡SiO—Si≡ | H$_3$SiO—SiH$_3$ | 5.63$_2$ |
|  | (HO)$_3$SiO—Si(OH)$_3$ | 6.59$_6$ |
| C—Si≡ | H$_3$C—Si(CH$_3$)$_3$ | 4.06$_3$ |
|  | H$_3$C—Si(OH)$_3$ | 4.31$_4$ |
|  | H$_3$C—Si(OSiH$_3$)$_3$ | 4.38$_3$ |
|  | (HO)$_3$SiH$_2$C—Si(OH)$_3$ | 4.65$_1$ |

Note)
Numerical values in Table 1 are dissociation enthalpies at the G2 level of theory obtained this time, and the numerical value within parenthesis is dissociation enthalpy at the G2 level of theory described in J. Phys. Chem., vol. 97, p. 8207 (1993).

The results show that the strength of the Si—O bond increases with progressing oxidation of back bonds of Si and, in the case of complete oxidation, reaches about 6.6 eV/Si—O. On the other hand, the influence of oxidation of back bonds of Si on the strength of the Si—C bond is smaller than those on the strength of the Si—O bond. Even after complete oxidation of the back bonds, the strength of the Si—C bond is 4.7 eV/Si—C at the highest, and this value is lower by about 2 eV than the strength of the Si—O bond. The results shown in FIG. 10 clearly explain a difference in deformation properties between the oxygen cross-linkage determined by both the flexibility of Si—O—Si angle deformation and the hardness of Si—O bond stretch and the carbon cross-linkage determined by both the hardness of the X—C—X angle deformation and the softness of X—C bond stretch (X=Si or C). For comparison, the result of potential energy plane for the bond angle deformation of an $sp^3$ hybrid single bond in C—C—C bonding similar to that in diamond which is the well-known hardest material is shown in FIG. 8. It is apparent that the potential plane is steepest within an elastic deformation range.

Figure 9:
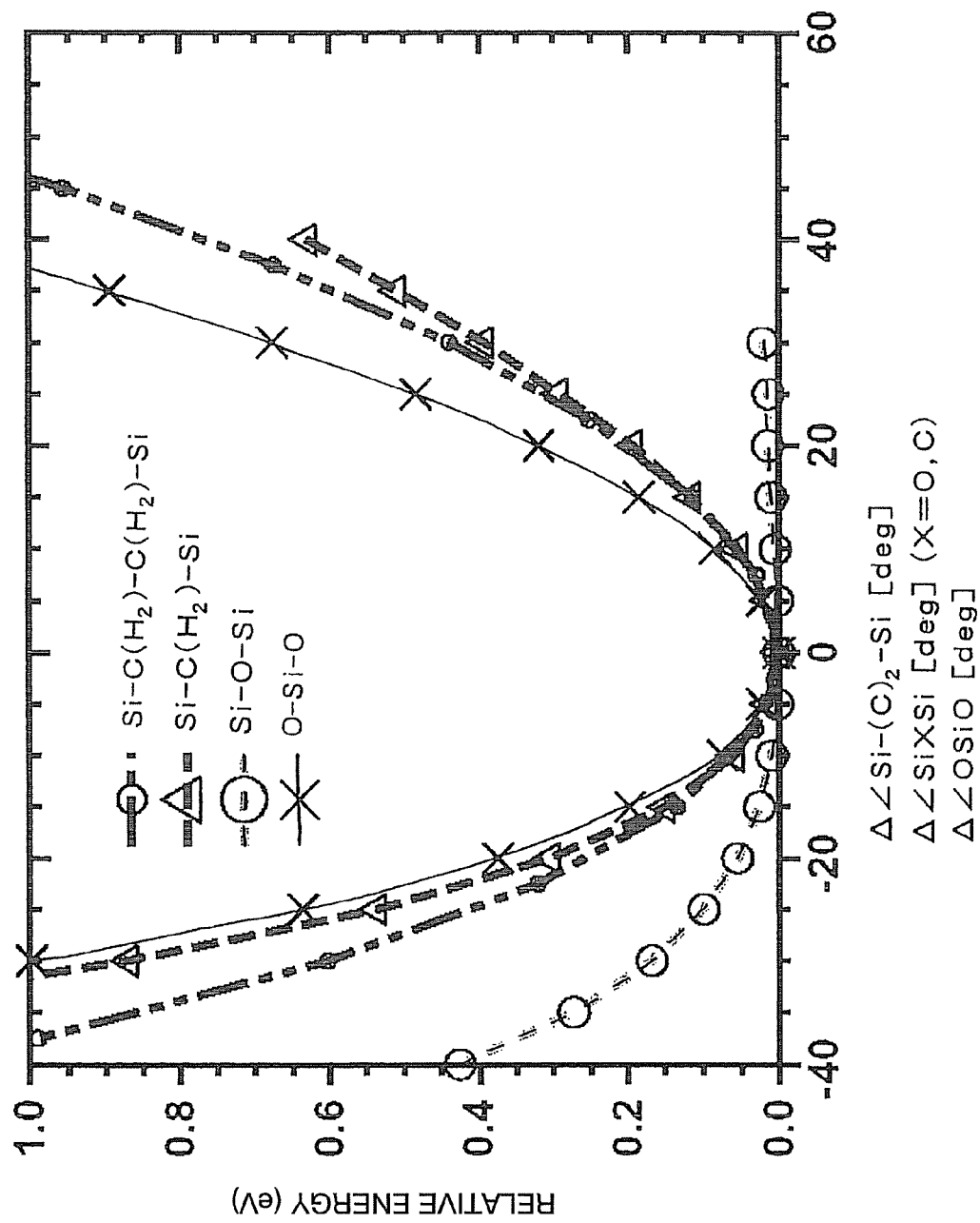
FIG. 9 is a graph showing a change in potential energy curves for characteristic distortions in various types of cross-linkages along with an ethylene-linkage as conventional examples.

FIG. 9 is a graph showing a change in potential energy curves for characteristic distortions in various types of cross-linkages along with an ethylene cross-linkage (Si—CH$_2$—CH$_2$—Si) disclosed also in reference 2. Of course, in the ethylene cross-linkage, twice of deformation energy is necessary for deforming both two equivalent bond angles Si—C—C and C—C—Si between the Si atoms by some amount compared with that for deforming the bond angle Si—C—Si in the methylene cross-linkage Si—C—Si by just the same amount. In fact, however, the total angle deformation amount can be divided between the two bond angles in the cease of the ethylene cross-linkage. Accordingly, the potential energy curve for the characteristic distortions on a wide-angle side becomes merely somewhat stiffer than that in the methylene cross-linkage.

Figure 11B:
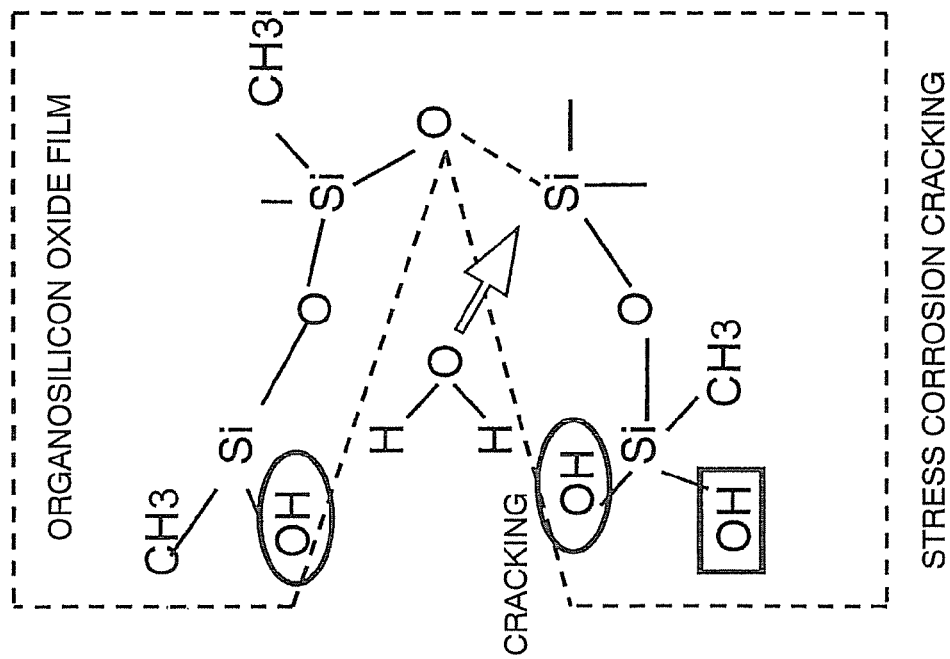
FIGS. 11A and 11B are schematic diagrams showing a mechanism of stress corrosion cracking in an organosilicon oxide film.
Figure 11A:
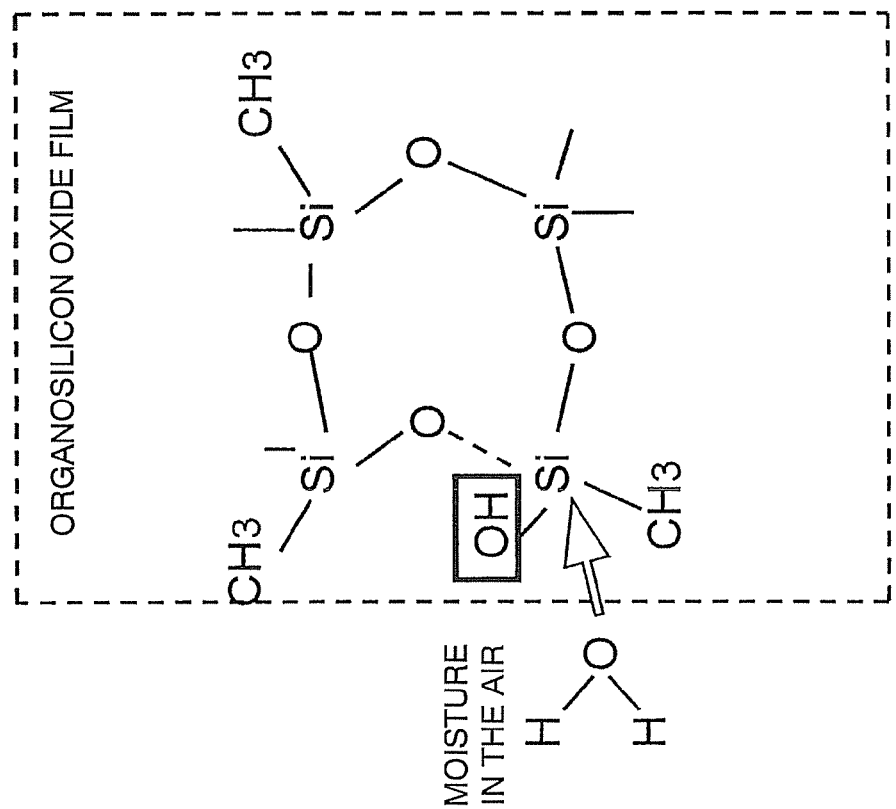

It has been found that the hardness of an ethylene cross-linkage is not so different from the that of a methylene cross-linkage. On the other hand, a significant difference in the gap (i.e. pore) formation is brought about regarding moisture absorption and stress corrosion cracking attributable to moisture absorption. A mechanism through which hygroscopic moisture accelerates stress corrosion cracking (progress of cracking) is shown in FIGS. 11A and 11B.

In general, regardless of film formation methods, uncross-linked sites still remain in the organosilicon oxide film. Accordingly, residual tensile stress is involved in the film to cause a cross-linking reaction and thus to cause self-shrinking. Moisture in the air causes a hydrolysis reaction with a distorted Si—O—Si bond present at the front end of crack in the organosilicon oxide film (FIG. 11A). The reason for this is that Si is an element which is likely to take a hypervalent state, and O in hygroscopic moisture (H$_2$O) causes a nucleophilic reaction preferentially with the Si at the distorted Si—O bond by tensile stress. As a result, an original distorted Si—O—Si bond is cleaved to form two Si—OH groups (FIG. 11B). The cleaving reaction proceeds in a chain reaction at the front end of crack by moisture absorbed from atmosphere. The progress of the cracking divides the organosilicon oxide film into fine domains. Thus, the cleaved organosilicon oxide film is locally shrunk to relax the tensile stress inherently generated in the film. The resultant Si—OH group accelerates breakage of the cross-linkage structure. Further, since the Si—OH group is a polar group, it accelerates hydrogen bond formation resulting in adsorption of further H$_2$O molecules. And also, since it is a polar group which produces an orientation polarization, the dielectric constant is disadvantageously increased by itself and by adsorption of further H$_2$O molecules. Accordingly, in order to suppress stress corrosion cracking, not only the stress relaxation but also the suppression of the hygroscopicity of the film is important.

Figure 12A:
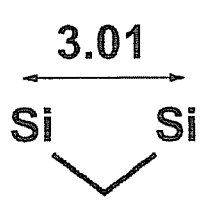
FIGS. 12A to 12G are diagrams showing a comparison of gap sizes and sizes of water monomer and dimmer for hygroscopic moisture attributable to various cross-linkages structures.
Figure 12B:
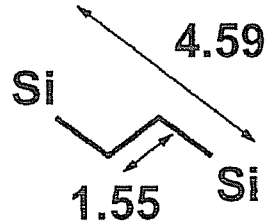
Figure 12C:
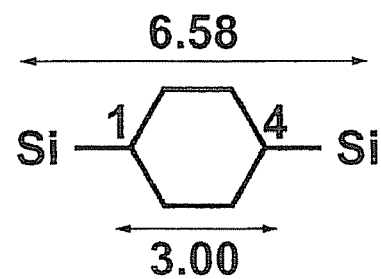

FIGS. 12A to 12G are diagrams showing a comparison of gap sizes and sizes of water monomer and dimmer for hygroscopic moisture attributable to various cross-linkage structures. FIG. 12A stands for a methylene cross-linkage, FIG. 12B for an ethylene cross-linkage, FIG. 12C for a phenylene cross-linkage, FIGS. 12D and 12E for cyclobutane cross-linkages according to this embodiment, FIG. 12F for an H$_2$O monomer, and FIG. 12G for an H$_2$O dimer, respectively. The arrows and the values attached to each arrow in FIGS. 12A to 12G indicate the distance between atoms related to the gap size.

As can be seen from FIGS. 12A to 12G, the gap size of the methylene cross-linkage site is smaller than the size of the $H_2O$ dimmer. On the other hand, it can be understood that, for the ethylene cross-linkage site and the phenylene cross-linkage site, disadvantageously, the gap size is larger than the size of the $H_2O$ dimer. This brings about the situation such that two or more $H_2O$ molecules can act on the distorted Si—X bond moiety.

Figure 13:
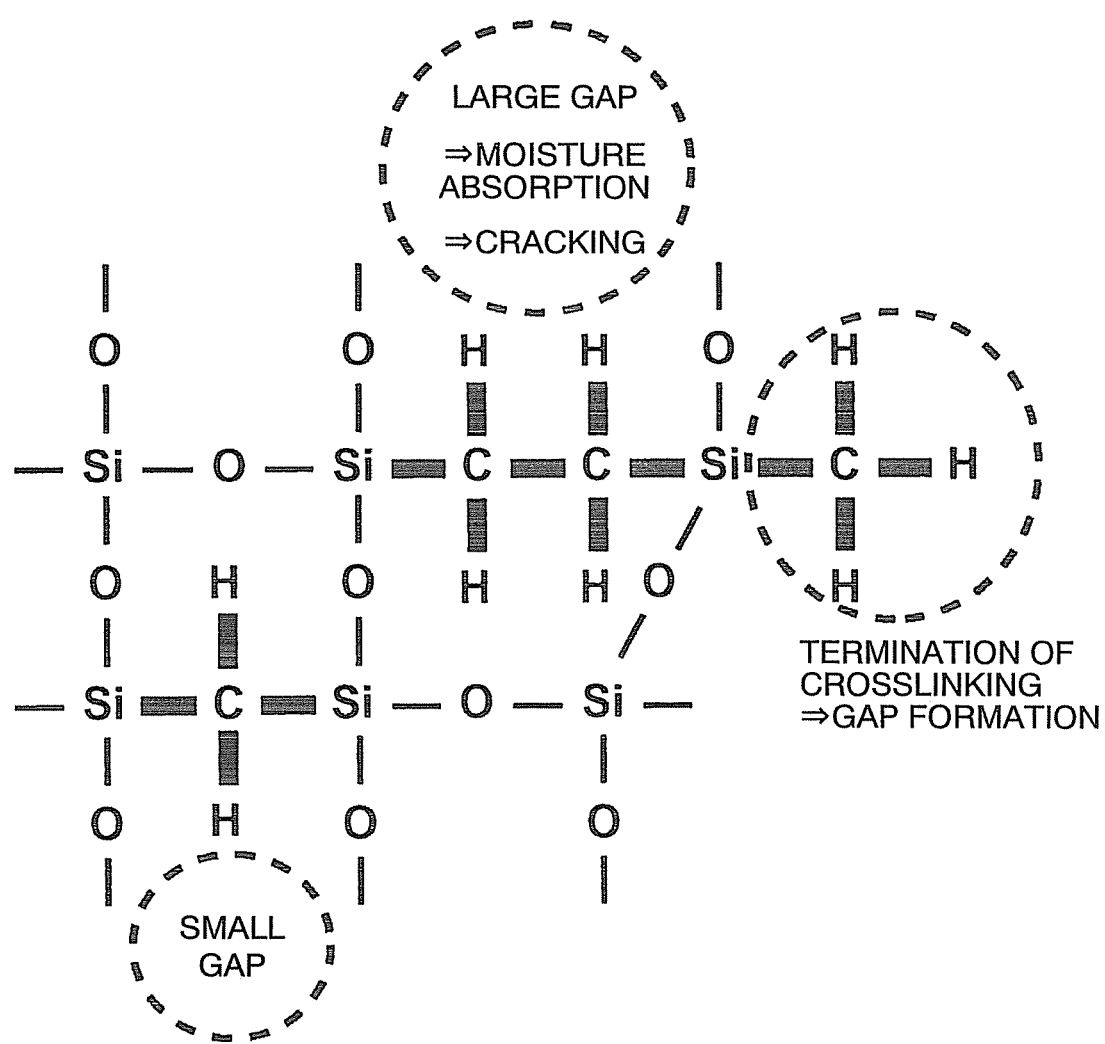
FIG. 13 is a schematic diagram showing a difference in hygroscopic deterioration derived from a difference in gap sizes between a methylene-linkage, an ethylene-linkage, and a methyl-termination.

FIG. 13 is a schematic diagram showing a difference in hygroscopic deterioration derived from a difference in gap sizes between a methylene cross-linkage, an ethylene cross-linkage, and a methyl-termination. Not only in a methyl group or the like which terminates the cross-linkage but also in an ethylene cross-linkage having a large gap size, upon arrival of hygroscopic moisture at the gap, cracking occurs when tensile stress is induced to this part. On the other hand, in the methylene cross-linkage, the gap size is inherently so small that the moisture absorption itself is less likely to occur. By contrast, when the cyclobutane cross-linkage according to the embodiment is used, particularly when a suitable 1,2-position isomer (ortho-isomer) is used, the gap size can become smaller than that at the ethylene cross-linkage site. When a hydrophobic fluorine-substituted derivative or the like at the cyclobutane cross-linkage moiety is used, the moisture absorption can be further suppressed.

Figure 2:
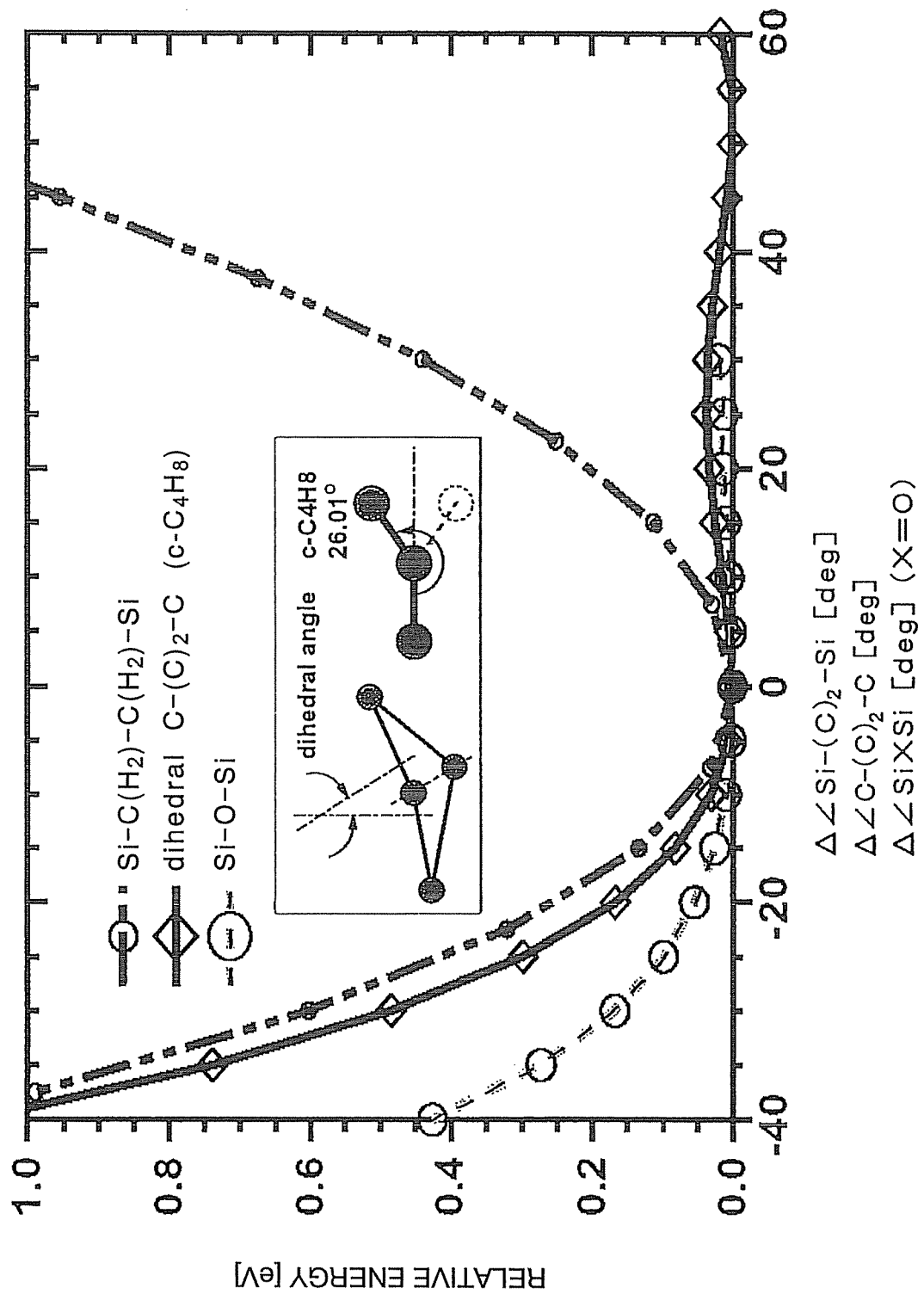
FIG. 2 is a graph showing a comparison of a change in potential energy curves for characteristic distortions between an isolated cyclobutane molecule and conventional linkage examples having an ethylene-linkage or an oxygen-linkage (siloxane skeleton)
Figure 5:
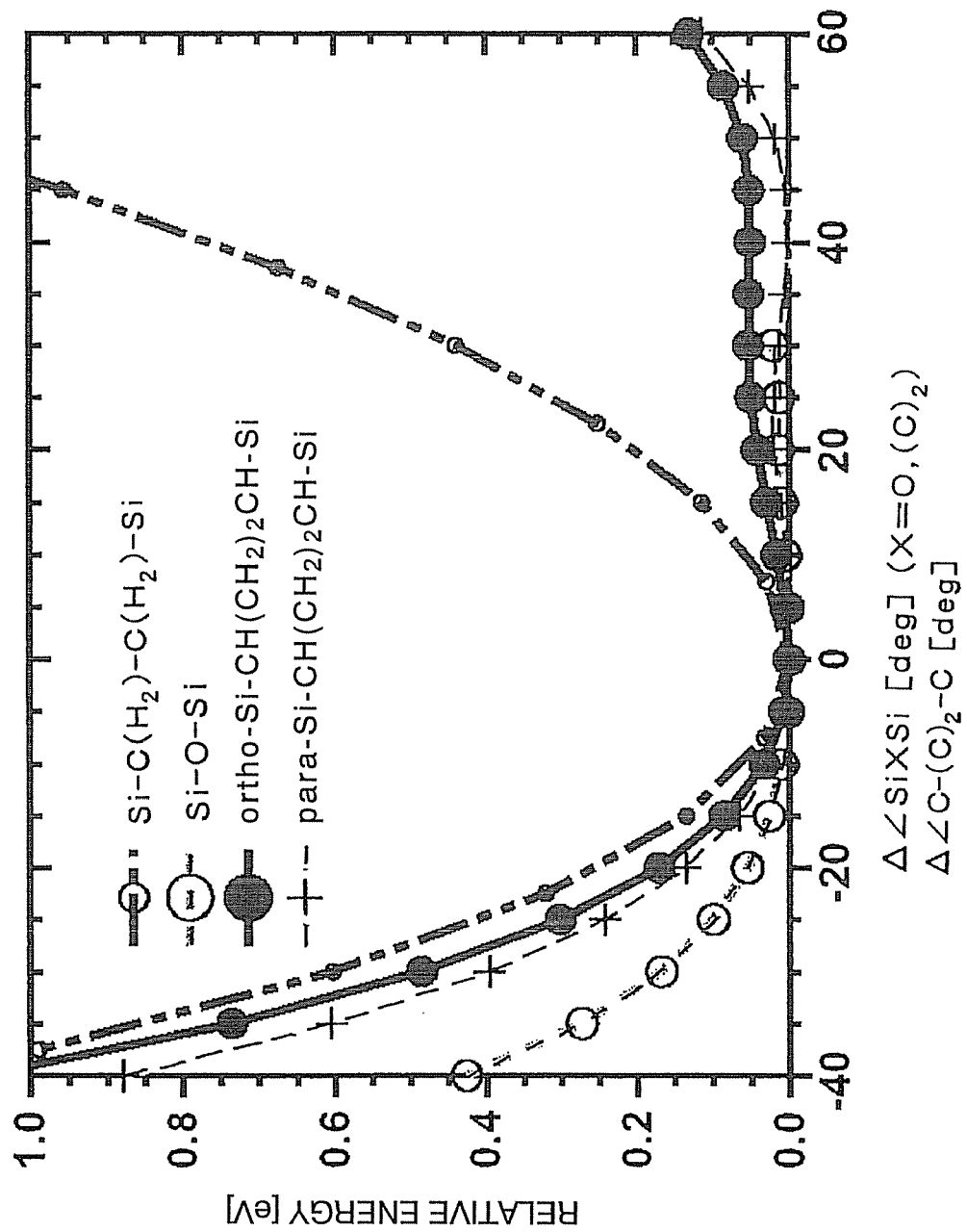
FIG. 5 is a graph showing a comparison of a change in potential energy curves for characteristic distortions between conventional linkage examples having an ethylene-linkage or an oxygen-linkage (siloxane skeleton) and the cross-linkage of trans-isomers in two types of the cyclobutane-linkage.

Next, the results of potential energy curves for characteristic distortions in the cyclobutane cross-linkage falling within the scope of the present invention will be compared with the potential energy curves for characteristic distortions in other types of cross-linkages as conventional examples. In order to clarify the essence of the effect of cyclobutane cross-linkage, a change in a potential energy curve for characteristic distortions of an isolated cyclobutane molecule (c-$C_4H_8$) per se, which corresponds to a prototype of cyclobutane cross-linkage, is compared with a change in a potential energy curve for characteristic distortions in a methylene cross-linkage as shown in FIG. 1, and is compared with a change in a potential energy curve for characteristic distortions in an ethylene cross-linkage as shown in FIG. 2. Since the C atom constituting cyclobutane is monovalent and, therefore, has an $sp^3$ hybrid orbital in a normal situation, a C—C—C bond angle in a stable state is to be around 109.5°. However, in order to form a four-membered ring, the bond angle should become around 90°. To relax the distortion as much as possible, the cyclobutane takes a structure, which is bent in a dog-leg form on C . . . C diagonals in the four-membered ring, rather than a planar structure. The bending angle is about 26° in terms of a dihedral angle. A change in the dihedral angle has been adopted as a variable of the potential energy curve for the bond angle deformation in cyclobutane cross-linkage. In FIGS. 1, 2 and 5, a change in dihedral angle in abscissa is plotted with permuted its signs so that comparison with Si—O—Si and so on can easily be made. That is, when the dihedral angle is larger than an equilibrium value (for example, 26° where the bending of the four-membered ring becomes large, a negative value is used while, when the dihedral angle is smaller than the equilibrium value where the four-membered ring becomes close to a planar configuration, a positive value is used.

As can be seen from FIGS. 1 and 2, the potential energy curves for characteristic distortions of cyclobutane behaves similar to that in oxygen cross-linkage (Si—O—Si) rather than those in a methylene cross-linkage (Si—C—Si) and an ethylene cross-linkage (Si—C—C—Si). In the oxygen cross-linkage, when the Si—O—Si bond angle is forced to bring to 180° or larger, substantially no energy loss occurs on its potential energy plane at a wide-angle side because of the bending into a reverse direction being possible. Just as with this case, in cyclobutane, when bending is made by the dihedral angle of 26°, a cyclobutane reaches a substantially planar configuration. Under a subsequent bending force, bending into a reverse direction merely occurs. Reflecting this, a change in the potential energy curves for the bond angle deformation is symmetrical about this dihedral angle of 26° as a symmetry axis. Taking a change in such a direction of increasing the dihedral angle also into consideration, a change in potential energy is kept small satisfactorily within a range for dihedral angle change of approximately (26°+ 10°)×2=72° in both distortional direction. That is, within the above distortion range, deformation for relax the internal/external stresses can be realized easily, and the structure can be said to be satisfactorily flexible.

Figure 4:
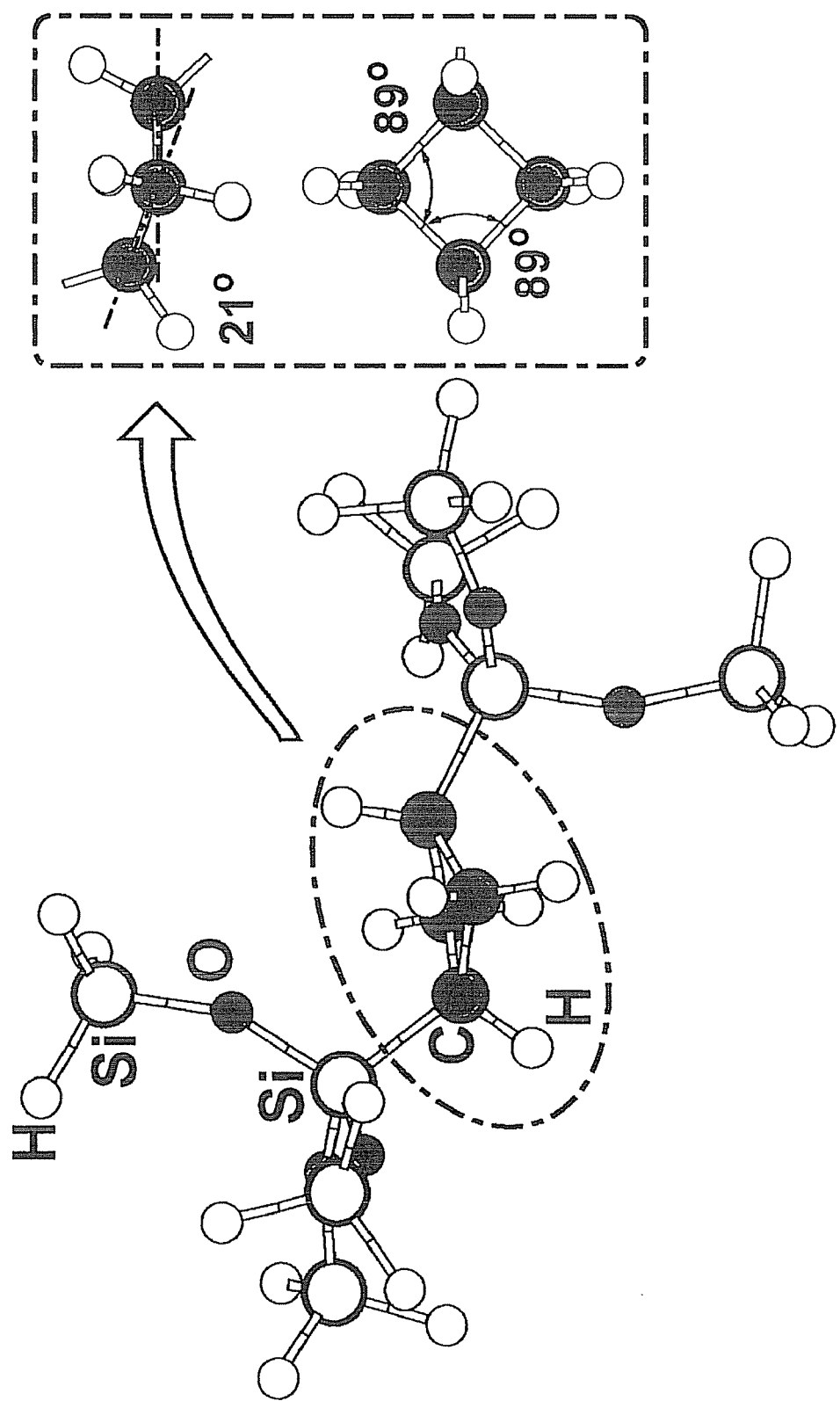
FIG. 4 is a molecular model for the para-position cross-linkage of trans-isomers in a cyclobutane cross-linked organosilicon oxide film.
Figure 12D:
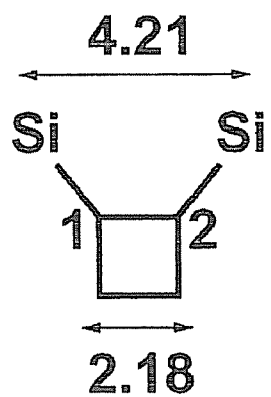
Figure 12E:
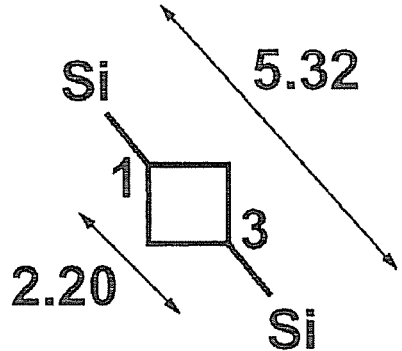
Figure 12F:
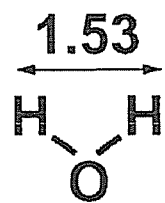
Figure 12G:
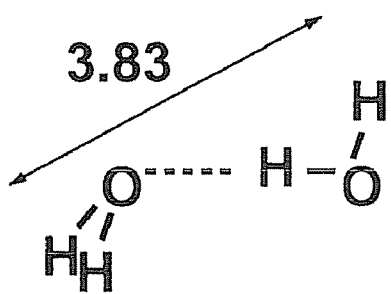

Next, the results will be described that the potential energy curves for characteristic distortions of the isolated cyclobutane molecule per se are also maintained in the cyclobutane cross-linkage. FIGS. 3 and 4 are diagrams showing model molecules of cyclobutane cross-linked organosilicon oxide films used in the calculations. In these drawings, structurally fully-relaxed most stable structures are shown. FIG. 3 shows model for the ortho-position cross-linkage of trans-isomers, and FIG. 4 shows model for the para-position cross-linkage of trans-isomers. As can be seen from FIG. 5, the ortho-position cross-linkage of trans-isomers and the para-position cross-linkage of trans-isomers are substantially identical to each other in C—C—C bond angle and dihedral angle in the cyclobutane cross-linkage moiety, and further are substantially identical in C—C—C bond angle and dihedral angle to the isolated cyclobutane molecule per se. When the gap size (pore size) in FIG. 12D is compared with the gap size in FIG. 12E, it can be said that the ortho-position cross-linkage of trans-isomers having a smaller gap size is more preferred than the para-position cross-linkage of trans-isomers.

Figure 6:
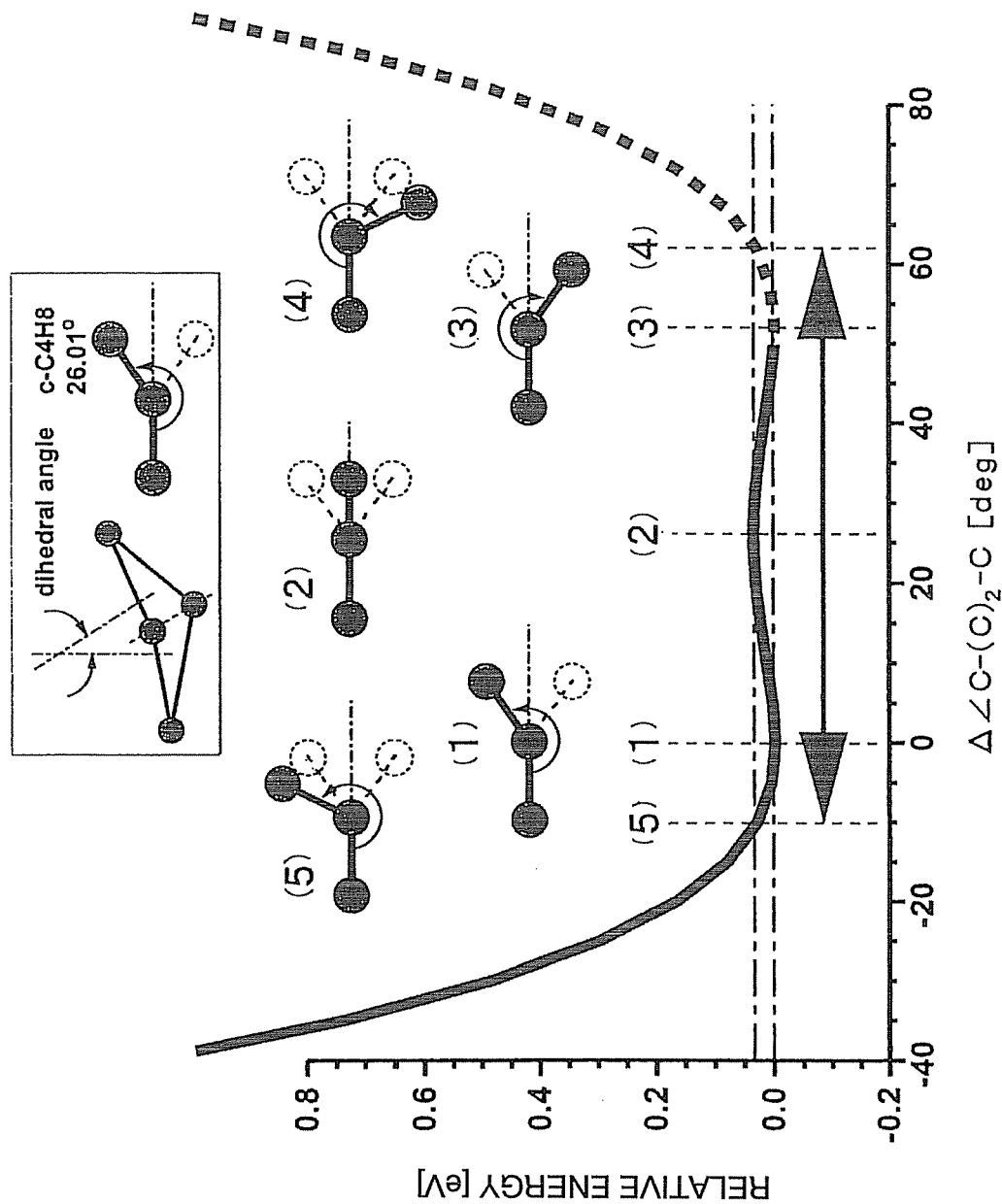
FIG. 6 is a graph showing a change in both a potential energy curve for a distortion of dihedral angle in cyclobutane cross-linkage and the structural changes at the linkage along the distortion.

FIG. 5 is a graph showing a comparison of a change in potential energy curves for characteristic distortions between an ethylene cross-linkage and a cyclobutane cross-linkage in this embodiment. FIG. 6 is a graph showing a change in potential energy curves for characteristic distortions in a cyclobutane cross-linkage in this embodiment together with schematic views for structural changes of cross-linkage moieties. As with the isolated cyclobutane molecule, in the cyclobutane cross-linkage, after bending by 26° (for the ortho-position cross-linkage of trans-isomers) or by 21° (for the para-position cross-linkage of trans-isomers) in terms of dihedral angle which renders the state substantially planar, bending into a reverse direction occurs. Reflecting this, a change in potential energy curves for the characteristic distortion is symmetrical about the above mentioned amount of angle deformations as a symmetrical axis (FIG. 6). Taking a change in such a direction of increasing the dihedral angle also into consideration, a change in potential energy is kept satisfactorily small within a range for dihedral angle change of approximately (26°+10°)×2=72° (for the ortho-position cross-linkage of trans-isomers) or approximately (21°+10°)× 2=62° (for the para-position cross-linkage of trans-isomers). That is, easy deformation is also possible for cyclobutane cross-linkage, and a satisfactorily flexible structure is realized. As shown in FIG. 5, this flexibility has never been observed in the ethylene cross-linkage.

For the reasons set out above, it can be said that a low-k insulating film formed of an organosilicon oxide film possessing excellent mechanical strength and, at the same time, possessing excellent dielectric properties can be formed by using the compositions for film formation in this embodiment.

Second Embodiment

Figure 14A:
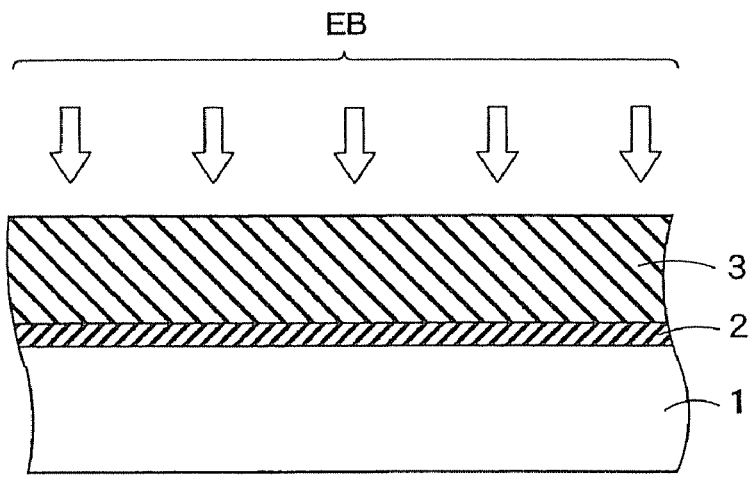
FIGS. 14A to 14C are schematic diagrams showing a production process of a semiconductor device in a second embodiment.
Figure 14B:
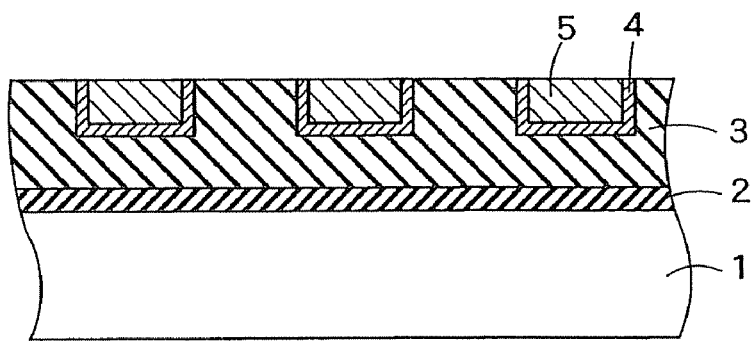
Figure 14C:
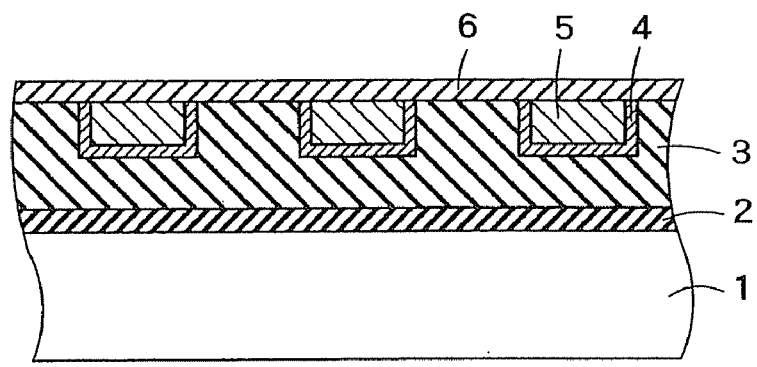

The second embodiment will be described with reference to the accompanying drawings. In this embodiment, an example of the formation of an interlayer insulating film in a semiconductor device using the compositions for film formation described in the first embodiment will be described. FIGS. 14A to 14C are schematic diagrams showing a production process of a semiconductor device in the second embodiment.

At the outset, as shown in FIG. 14A, a insulating film 2 is formed on a surface of a semiconductor substrate 1 with elements of semiconductor devices integrated thereon. An interlayer insulating film 3 is then formed on the substrate insulating film 2 by utilizing heating and electron beam irradiation. A specific method for forming the interlayer insulating film 3 will be described in detail later.

As shown in FIG. 14B, grooves for interconnects having desired size and shape are then formed at predetermined positions in the interlayer insulating film 3. A barrier metal 4 and a metallic interconnect 5 are formed within the grooves for interconnects, and the surface of the interlayer insulating film 3, the barrier metal 4, and the metallic interconnect 5 is flattened by a well-known CMP process. Here Cu interconnect composed mainly of Cu is used as the metallic interconnect 5.

Thereafter, as shown in FIG. 14C, a barrier insulating film 6 formed of SiN or SIC is formed on the flattened surface of the interlayer insulating film 3, the barrier metal 4, and the metallic interconnect 5.

The method for interlayer insulating film 3 formation will be described in detail. The interlayer insulating film 3 is formed through the following steps 1 to 4.

Step 1

Varnish is coated by spin coating on a semiconductor substrate 1. More specifically, a liquid source called varnish and prepared by dissolving a cyclobutane cross-linkage composition as a precursor of a material for a low-k insulating film in a solvent is spin coated with a spin coater on a surface of a substrate insulating film 2 provided on a semiconductor substrate 1 to form a coating film. For example, PGPE (propylene glycol monopropyl ether) can be used as the solvent.

Step 2

After the coating film is formed on the semiconductor substrate 1, the semiconductor substrate 1 is heat-treated at 80° C. for one min. Specifically, the semiconductor substrate 1 with the coating film formed thereon is placed on a hot plate placed within a reaction vessel for electron beam irradiation treatment and held at 80° C. This situation is held for one min. Thus, the coating film treatment is heat-treated at 80° C. for one min to remove the solvent in the coating film.

Step 3

After the heat treatment, the semiconductor substrate 1 is heat-treated at 200° C. or above and 350° C. or below for one min. Specifically, in such a situation that the semiconductor substrate 1 is placed on the hot plate, the temperature of the hot plate is held at 200° C. This situation is held for one min. Thus, the coating film is heat-treated at 200° C. for one min within the reaction vessel for electron beam irradiation treatment, whereby the compounds including the compositions for film formation contained in the coating film is cross-linked and, at the same time, the coating film is bonded (anchored) onto the semiconductor substrate 1. This step is preferably carried out in an oxidizing atmosphere unless a metallic interconnect, which is likely to be oxidized, is exposed.

Step 4

After the heat treatment, the semiconductor substrate 1 is subjected to electron beam irradiation treatment in an evacuated atmosphere while heating the semiconductor substrate 1 at 400° C. or above and 600° C. or below to form an interlayer insulating film 3. Specifically, about 20 slm of nitrogen is introduced into the reaction vessel and the vessel is evacuated at a preferred pressure. In such a situation that the semiconductor substrate 1 is placed on a hot plate held at 400° C. in an evacuated nitrogen atmosphere, electron beams are irradiated to the coating film to form an interlayer insulating film 3. Upon exposure of the coating film to the electron beams, chemical bonds of oxygen molecules, water molecules, and hydroxyl groups in the coating film are broken, whereby the coating film is oxidized automatically to a suitable extent by the produced oxidizing species. This step is preferably carried out in a non-oxidizing atmosphere to suppress excessive and undesired oxidation of the coating film. Such excessive oxidation results in removal of carbon-related groups in the film and deterioration of dielectric properties in the film.

In the electron beam irradiation at step 4, in this embodiment, the pressure within the reaction vessel is preferably varied at two stages of about $5.5 \times 10^3$ Pa (40 Torr) and about $8.0 \times 10^3$ Pa (60 Torr). Specifically, preferably, for about 90 sec from the start of electron beam irradiation, electron beam irradiation is performed in such a state that the pressure within the reaction vessel is maintained at $5.5 \times 10^3$ Pa and the amount of incident electrons per unit time (hereinafter referred to as "exposure dose") is about 5 mC/cm$^2$·sec, and, for a period from that to the completion of the electron beam irradiation, that is, for about 30 sec, the electron beam irradiation is carried out in such a state that the pressure within the reaction vessel is $8.0 \times 10^3$ Pa and the exposure dose is about 4 mC/cm$^2$·sec. Preferably, the energy of the electron beams is, for example, within the range from 1 to 15 keV. The total amount of the electrons incident on the semiconductor substrate (hereinafter referred to as "total exposure dose" or "fluence") was 500 mC/cm$^2$. The total exposure dose is not limited to the above value and may be any value that does not cause deterioration in the cyclobutane cross-linked organosilicon oxide film, and may be any value depending on the film thickness.

What is to be noted here is that various parameters such as the pressure within the reaction vessel or the exposure dose are varied while heating the semiconductor substrate 1 during exposure of the interlayer insulating film 3 to electron beams, whereby an interlayer insulating film 3 having a low dielectric constant and a satisfactory mechanical strength is provided.

In this embodiment, at step 4, both the pressure and the exposure dose are varied. Even when any one of the pressure and the exposure dose is varied, an insulating film having a high mechanical strength and a low dielectric constant can be realized.

Further, an insulating film having a high mechanical strength and a low dielectric constant can also be realized by varying one of parameters other than the pressure and the exposure dose. Parameters other than pressure and exposure dose are the temperature of the semiconductor substrate 1, the species of gases to which the semiconductor substrate 1 is exposed, the flow rate of the gases to be introduced into the reaction vessel, and the position of the semiconductor substrate 1. For example, the same effect can be attained by, at step 4, changing the temperature from 400° C. to 200° C., changing the gas species from nitrogen to argon, changing the gas flow rate from 25 slm to 3 slm, or changing the position of the semiconductor substrate 1 measured from the inlet of the electron beam into the vessel from 50 mm to 120 mm.

In this case, however, the same effect sometimes cannot be attained depending, for example, upon the required mechanical strength and dielectric constant. Accordingly, in general, varying plural parameters simultaneously is preferred. The same effect as in this embodiment can be attained by varying plural parameters other than pressure and exposure dose or by varying any one of pressure and exposure dose and at least one of parameters other than pressure and exposure dose.

Specifically, the effect as described in this embodiment can be attained by varying at least one of the pressure within the reaction vessel, the temperature of the semiconductor substrate 1, the gas species to which the semiconductor substrate 1 is exposed, the flow rate of the gases to be introduced into the reaction vessel, the position of the semiconductor substrate 1, and the exposure dose at which the semiconductor substrate 1 is exposed.

Third Embodiment

Figure 15A:
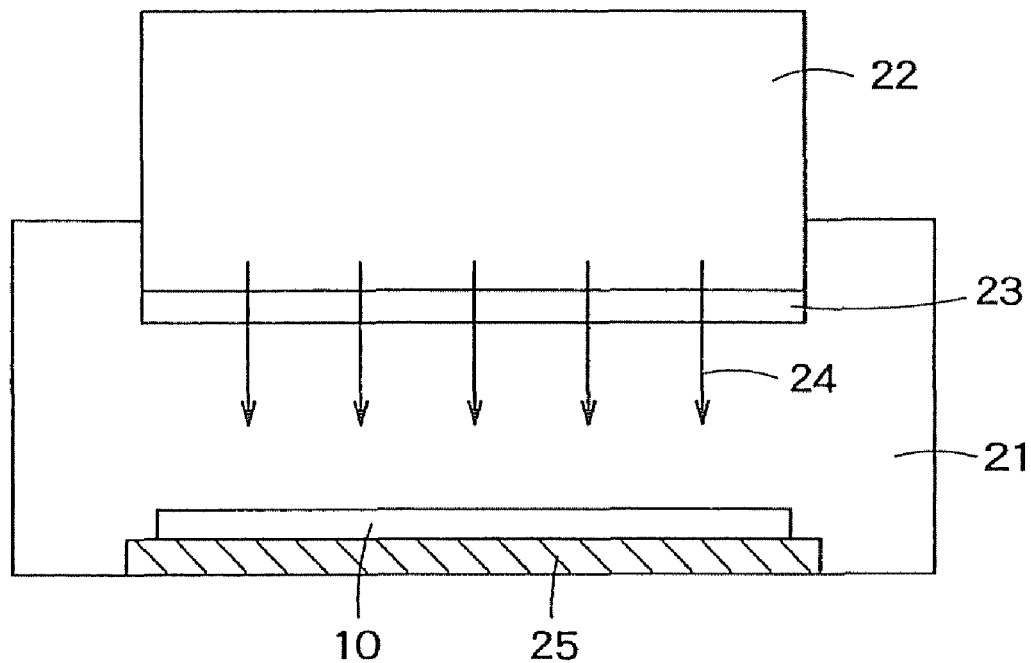
FIGS. 15A and 15B are schematic configuration diagrams showing electron beam irradiation apparatuses used in a third embodiment.
Figure 15B:
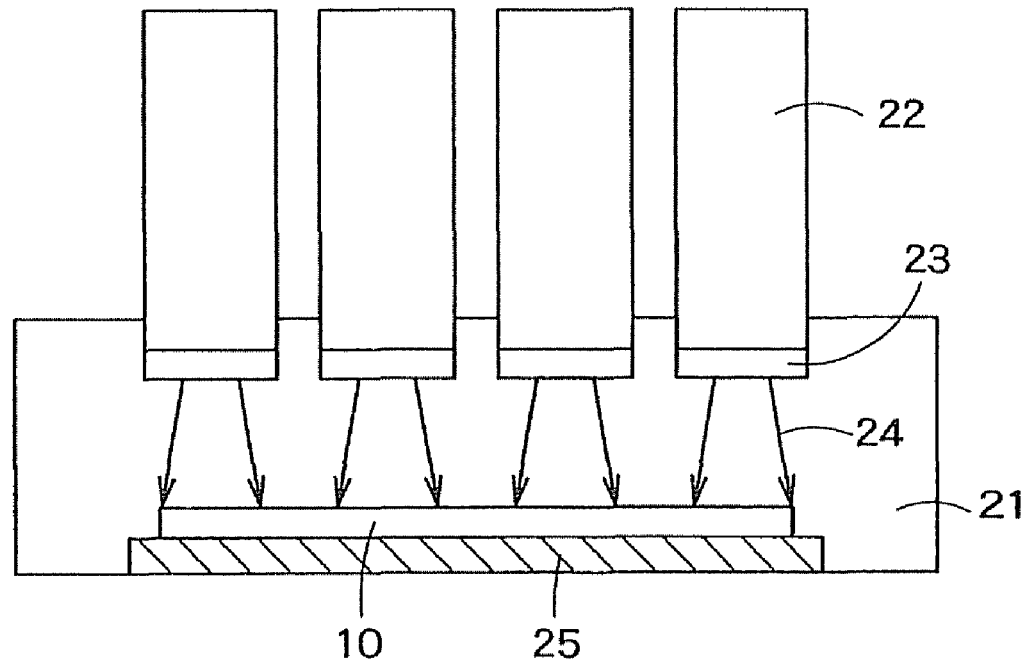

The third embodiment will be described with reference to the accompanying drawings. In this embodiment, a method for applying electron beams in the formation of the interlayer insulating film in the semiconductor device using the compositions for film formation described in connection with the first embodiment will be described. This embodiment is characterized by an electron beam irradiation step different from the electron beam irradiation step used in the second embodiment. Prior to the description of this embodiment, an electron beam irradiation apparatus used in this embodiment will be described. FIGS. 15A and 15B are schematic configuration diagrams showing electron beam irradiation apparatuses used in the third embodiment.

As shown in FIG. 15A, at least one electron beam generating part 22 is equipped at the upper part of a reaction vessel 21 in an electron beam irradiation apparatus in this embodiment. As shown in FIG. 15B, plural electron beam generating parts 22 may be provided for uniform irradiation overall the interlayer insulating film.

The electron beam generating part 22 is separated from the reaction vessel 21 by a partition wall 23. Electron beams 24 emitted from the electron beam generating part 22 is passed through the partition wall 23 and is introduced into the reaction vessel 21. A hot plate 25 is equipped in a lower part within the reaction vessel 21 so as to face the lower part of the electron beam generating part 22.

A semiconductor substrate 10 with a coating film formed thereon is placed on the hot plate 25. The semiconductor substrate 10 is irradiated with electron beams 24 under desired conditions. The hot plate 25 is connected to a control unit, and the control unit maintains the hot plate 25 at a desired temperature. The use of the hot plate 25 can allow the semiconductor substrate 10 placed on the hot plate 25 to be held at a substantially even temperature overall a substrate 10 and thus can realize even treatment.

An electron beam irradiation apparatus using gas-plasma as an electron beam source is generally adopted. Electrons generated in the plasma are withdrawn into the reaction vessel through a mesh, and the electron beam generating part and the reaction vessel are always in an identical atmosphere. Therefore, when a gas containing organic species is evolved from the film during its treatment by electron beam irradiation, the pressure in a discharge region in the electron beam generating part 22 rapidly and non-uniformly varies. Upon the undesired change in the pressure in the discharge region, the plasma discharge becomes unstable, and, consequently, the electron beam source becomes unstable. As a result, even electron beam irradiation is impossible. Accordingly, this apparatus has a possibility of posing a problem that a scattering, for example, in properties of the film after annealing accompanied with electron beam irradiation, for example, a scattering in dielectric constant and mechanical strength, occurs.

By contrast, in the electron beam irradiation apparatus used in this embodiment, a partition wall 23 is provided between the electron beam generating part 22 as the electron beam source and an object to be irradiated (i.e. the semiconductor substrate 10 with the coating film formed thereon), and an electron beam 24 is irradiated through the partition wall 23 to the object. Therefore, the influence of gases evolved from the object on the electron beam generating part 22 can be suppressed by the partition wall 23. Consequently, an electron beam 24, which is kept even spatially and with the elapse of time, can be irradiated to the object, whereby a scattering in properties of the film after annealing accompanied with electron beam irradiation can be reduced.

Figure 16A:
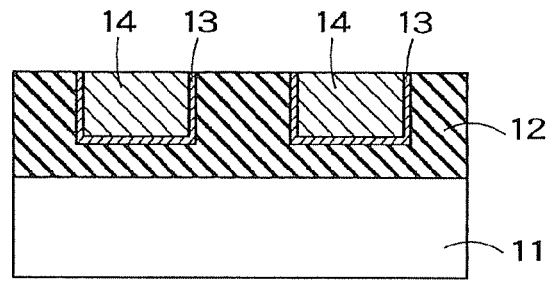
FIGS. 16A to 16C are schematic diagrams showing a production process of a semiconductor device in a third embodiment.
Figure 16B:
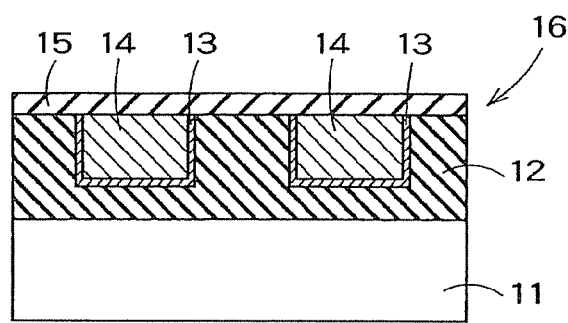
Figure 16C:
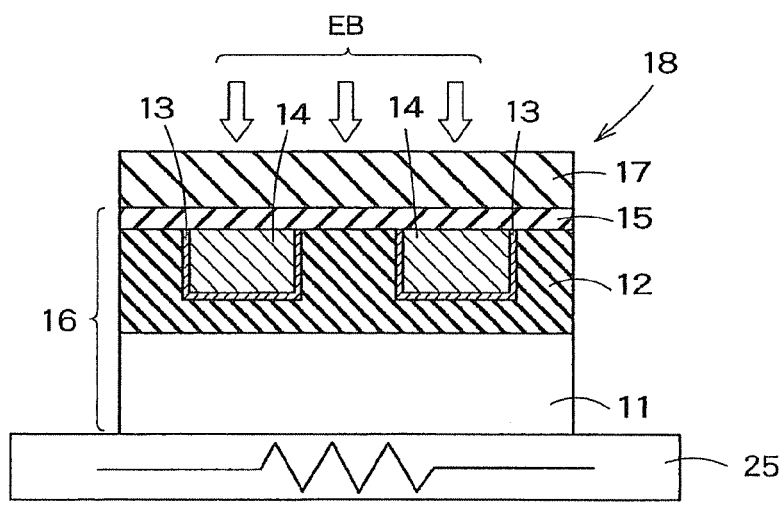

Next, an example of the production of a semiconductor device using the above electron beam irradiation apparatus will be described. FIGS. 16A to 16C are schematic diagrams showing a production process of a semiconductor device in a third embodiment of the present invention.

At the outset, as shown in FIG. 16A, a substrate insulating film 12 is formed on a surface of a semiconductor substrate 11. Here a TEOS film or, maybe, an organosilicon oxide film formed using the compositions for film formation in the first embodiment is used as a substrate insulating film 12. Subsequently, grooves for interconnects having desired size and shape are formed at predetermined positions on the surface side of the substrate insulating film 12. Thereafter, a barrier metal 13 and a copper (Cu) interconnect 14 composed mainly of and Cu are formed within the grooves for interconnects by a well-known CMP process, and the surface of the substrate insulating film 12, the barrier metal 13, and the Cu interconnect 14 is flattened.

Next, as shown in FIG. 16B, a silicon nitride film 15 as a barrier insulating film is formed on the flattened surface of the substrate insulating film 12, the barrier metal 13, and the Cu interconnect 14. The assembly, in which elements up to the silicon nitride film 15 are formed on the semiconductor substrate 11, is referred to as a first layer semiconductor substrate 16.

After the formation of the silicon nitride film 15, as shown in FIG. 16C, an interlayer insulating film 17 with a low-k, which is a cyclobutane cross-linkage organosilicon oxide film, is formed on the silicon nitride film 15 using the compositions for film formation described above in connection with the first embodiment.

The method for forming the interlayer insulating film 17 will be described in more detail. The interlayer insulating film 17 is formed through the following steps 1 to 4.

Step 1

Varnish prepared by dissolving the cyclobutane cross-linkage compositions for film formation, described above in connection with the first embodiment, as a precursor of the low-k insulating film material is supplied on the surface of the silicon nitride film 15. In this embodiment, the varnish is supplied by a coating method which can supply the varnish evenly to a substantially even thickness to form a good cyclobutane cross-linkage organosilicon oxide film. Specifically, in the varnish coating, the varnish is coated on the surface of the silicon nitride film 15, for example, by spin coating, which is one of coating methods, with a coater (not shown) as a coating device.

Step 2

As shown in FIG. 16C, in such a state that the silicon nitride film 15 with the varnish coated thereon faces upward, the first layer semiconductor substrate 16 is first placed on a hot plate 25 (a heating device) as a temperature controller. Thereafter, the varnish together with the first layer semiconductor substrate 16 is heated while regulating the temperature of the hot plate 25 so that the temperature of the varnish is held at about 80° C., and this situation is held for about one min, whereby first heat treatment of the varnish is performed.

Step 3

In such a situation that the first layer semiconductor substrate 16 is placed on the hot plate 25, the varnish together with the first layer semiconductor substrate 16 is heated while regulating the temperature of the hot plate 25 so that the temperature of the varnish is held at 200° C., and this situation is held for about one min. Thus, second heat treatment of the varnish is performed. As a result of the heat treatment in step 2 and the heat treatment in step 3, the solvent contained in the varnish is removed by evaporation, and the varnish (coating film) is bonded (anchored) onto the silicon nitride film 15.

According to experiments conducted by the present inventors, it has been found that the adoption of the heating method as in steps 2 and 3, in which the temperature of the varnish is raised stepwise, can allow components (for example, solvent) other than the cyclobutane cross-linkage compositions for film formation as a main component of the cyclobutane cross-linked organosilicon oxide film in the varnish to be substantially completely evaporated with high efficiency, whereby the coating film can be effectively fixed physically and chemically.

Step 4

The first layer semiconductor substrate 16 is placed on the hot plate 25 and, in this situation, is placed in an atmosphere evacuated to about $1.3 \times 10^3$ Pa (10 Torr) so that the varnish and the cyclobutane cross-linked organosilicon oxide film formed from the varnish are not oxidized. Further, the atmosphere in which the first layer semiconductor substrate 16 is placed is filled with a gas composed mainly of a $H_2$ gas having reduction abilities. In performing electron beam irradiation which will be described later, the $H_2$ gas cleans the surface of the Cu interconnects 14, specifically cleans the oxides of the surface of the Cu interconnects, and suppresses the oxidation of the surface.

In this situation, the temperature of the hot plate 25 is regulated so that the temperature of the varnish is kept at about 400° C. to heat the varnish together with the first layer semiconductor substrate 16. Further, as indicated by an arrow in FIG. 16C, an electron beam with its irradiation (accelerated) energy of about 10 keV and its total exposure dose of about 500 mC/cm² is applied from an electron beam irradiation apparatus (not shown) toward the varnish.

In this case, the heating together with the electron beam irradiation situation are held for about 5 min. Thus, an interlayer insulating film 17 of a cyclobutane cross-linked organosilicon oxide film is formed on the surface of the silicon nitride film 15, in details, on the uppermost layer of the first layer semiconductor substrate 16.

As described above, only in step 4 as the final step among steps 2 to 4, the electron beam is irradiated toward the varnish while heat treating the varnish. This is adopted in order to prevent such a phenomenon that the irradiation of electron beams to the varnish without being fixed (bonded) on the silicon nitride film 15 leads to also an undesired deterioration of the low-k interlayer insulating film. In details, the undesired deterioration is that the irradiation of electron beams to the un-fixed varnish also influences on such components other than the cyclobutane cross-linkage compositions as the solvent of the varnish, and as a result, the deteriorated components resides in the film and a low-k interlayer insulating film having undesired properties is formed. That is, the reason why the application of the electron beam irradiation is limited only in step 4 is that a low-k interlayer insulating film having desired properties can be formed only by this process sequence.

Studies have been made on such conditions of the application of electron beam irradiation to the varnish in step 4 that an interlayer insulating film 17 can be formed by a desired cyclobutane cross-linked organosilicon oxide film in order to realize proper operation of a semiconductor device 18 in practical use. As a result, it has been found that the following conditions are useful.

At the outset, heat treatment is performed so that the temperature of the varnish is kept at a substantially constant temperature in the range of 200° C. or above and 500° C. or below, preferably in the range of about 380° C. to about 400° C., preferably 400° C.

Alternatively, electron beam irradiation may be performed in such a condition that the total exposure dose of the electron beams applied is set to a substantially constant value of not less than 300 mC/cm² and not more than 1000 mC/cm², preferably 500 mC/cm².

Alternatively, electron beam irradiation may be performed in such a condition that the accelerated energy of electron beams applied is set to a substantially constant value in the range of from about 1 keV to 15 key, preferably 10 keV.

Further, in this step, the semiconductor substrate with the varnish coated thereon is placed in an evacuated atmosphere in a given vacuum range in a gas having predetermined reduction abilities from the viewpoints of suppressing both the excess oxidation of the coating film and the oxidation of interconnects when metallic interconnects including of easily-oxidized elements such as Cu is surface-exposed. In particular, the semiconductor substrate with the varnish coated thereon is placed in the above a gas composed mainly of a $H_2$ gas in such an atmosphere that the vacuum pressure is set to a substantially constant value of from 6.67 Pa (0.05 Torr) to 66.7 Pa (0.5 Torr), preferably of 13.3 Pa (0.1 Torr).

Under such conditions, even after the completion of steps up to step 4, the oxidation of the surface of the Cu interconnects 14 is not observed, and an increase in specific resistivity after the interlayer insulating film 17 formation process compared with the specific resistivity before the interlayer insulating film 17 formation is only less than 3%. Further, in the steps up to step 4, separation (i.e. peeling-off) of the substrate insulating film 12, the barrier metal 13, the Cu interconnect 14, the silicon nitride film 15, and the interlayer insulating film 17 has not occurred at all.

As described above, in this embodiment, owing to the simultaneous steps of heat treatment and the electron beam irradiation treatment, the time necessary for completing steps 1 to 4 is as short as about 7 min. That is, the time necessary for the film forming step involving the evaporation of the solvent and the cross-linking reaction of the precursor can be reduced significantly, which takes about 30 min to one hr in the step of forming an insulating film only by heat treatment using the hot plate according to a conventional technique.

Further, in this embodiment, the required process temperature during the simultaneous heating and the electron beam irradiation in steps 1 to 4 can be decreased, for example, as described above, to 400° C., or to 500° C. or below as the upper limit. That is, in the step of forming an insulating film only by heat treatment using a hot plate according to a conventional technique, i.e., in so-called BEOL (back end of line)

process, the annealing temperature should be 500° C. or above, whereas, in this embodiment, the annealing temperature in the film annealing step can be decreased.

Accordingly, in this embodiment, owing to the simultaneous heating and electron beam irradiation, the interlayer insulating film 17 can be formed without causing significant deterioration such as oxidation or cracking, for example, of the interlayer insulating film 17 or the Cu interconnect 14. Thus, the grain growth of Cu in the Cu interconnect 14 during the film forming step can be suppressed, and the peeling-off at the interface between the Cu interconnect 14 and the silicon nitride film 15 can be suppressed.

Further, because the electron beams irradiation to the varnish is performed in an evacuated reducing gas atmosphere, the oxidation of the surface of the Cu interconnect 14 during the formation of the interlayer insulating film 17 can be suppressed to maintain the Cu interconnect 14 in a good electrical condition, i.e., to maintain the specific resistivity value of the Cu interconnect 14 at almost as low value as that before the film formation. The gas having reduction abilities may be gases other than the pure $H_2$ gas. In general, any gas, which can prevent the oxidation of the interconnect (here a Cu interconnect 14) and does not deteriorate the quality of a film formed (here an interlayer insulating film 17), may be used.

In this embodiment, the interlayer insulating film 17 in the semiconductor device 18 can be produced within a short process time. As a result, the production efficiency of the semiconductor device 18 can be enhanced, and the yield can also be improved.

Further, in this embodiment, also when a low-k insulating film consisting of cyclobutane cross-linked organosilicon oxide is used as the interlayer insulating film 17, the interlayer insulating film 17 can be formed in a short process time so that the interlayer insulating film 17 can be held in a good electrical and mechanical condition without sacrificing mechanical properties of strength. Therefore, the dielectric constant of the interlayer insulating film 17 in the semiconductor device 18 can be maintained at a desired good value, that is, at a low-k value. Accordingly, the electric capacity between interconnects of the semiconductor device 18 can be reduced, and the product of the interconnect resistance (R) and the capacity (C) between interconnects, that is, the so-called RC delay (wiring delay), can be reduced, whereby the operating speed of the semiconductor device 18 and, in its turn, the operating speed of various semiconductor devices using the semiconductor device 18, can be improved.

Further, a semiconductor device comprising a plural stacked interconnect layers (i.e. multilevel interconnections) may be produced by repeating the formation of individual layers such as a barrier metal 13, a Cu interconnect 14, a silicon nitride film 15, and an interlayer insulating film 17 on the substrate insulating film 12 in the same manner as described above, on the first layer semiconductor substrate 16. When this method is adopted, the formation of the multilevel interconnection layers does not cause deterioration in electrical properties such as interconnect resistance and capacity between interconnects. Accordingly, semiconductor devices having a high processing capability and, in its turn, various semiconductor devices having a high processing capacity using the semiconductor devices can be produced.

Fourth Embodiment

Figure 17A:
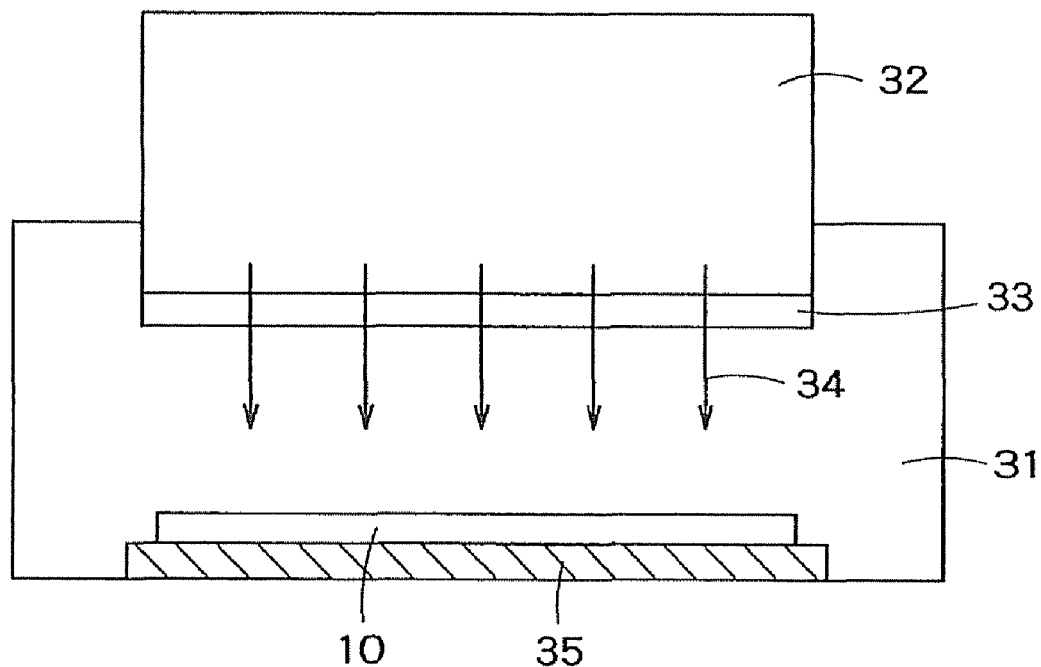
FIGS. 17A and 17B are schematic configuration diagrams showing ultraviolet photon irradiation apparatuses used in a fourth embodiment.
Figure 17B:
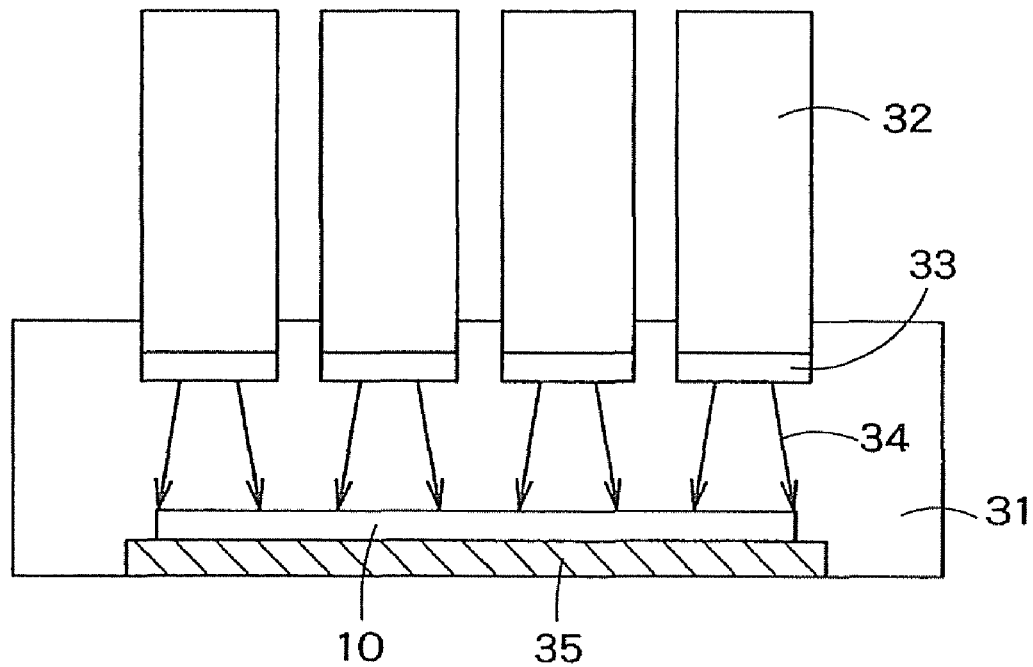

The fourth embodiment of the present invention will be described with reference to the accompanying drawings. In this embodiment, the method for ultraviolet light (i.e. ultraviolet photon) irradiation in the formation of an interlayer insulating film using the compositions for film formation described above in connection with the first embodiment will be described. Prior to the description of this embodiment, an ultraviolet photon irradiation apparatus used in this embodiment will be described. FIGS. 17A and 17B are schematic configuration diagrams of ultraviolet photon irradiation apparatuses used in the fourth embodiment. In the fourth embodiment, the overlapped description as the description in the third embodiment will be omitted.

As shown in FIG. 17A, at least one ultraviolet introduction part 32 is installed in the ultraviolet photon irradiation apparatus in this embodiment in its part which is the upper part of the reaction vessel 31. As shown in FIG. 17B, plural ultraviolet introduction parts 32 may be provided for uniform irradiation overall the interlayer insulating film. The ultraviolet introduction part 32 is separated from the reaction vessel 31 by a partition wall 33. Ultraviolet light 34 emitted from the ultraviolet introduction part 32 is passed through the partition wall 33 and is introduced into the reaction vessel 31.

The ultraviolet introduction part 32 is an apparatus, for example, a high pressure mercury lamp or an Xe excimer lamp, that can generate an ultraviolet light with its wavelength of from 120 nm to 400 nm, preferably a wavelength of not more than 242 nm, and can realize the irradiation of the ultraviolet light at a fluence of not less than 1000 mJ/cm$^2$ and not more than 10000 mJ/cm$^2$ in a practical time, preferably in from one min to 15 min. A semiconductor substrate 10 with a coating film formed thereon is placed on a hot plate 35, and ultraviolet light 34 is irradiated under desired conditions to the semiconductor substrate 10.

The ultraviolet photon irradiation apparatus is constructed so that a partition wall 33 is provided between the ultraviolet introduction part 32 as the ultraviolet source and an object to be irradiated (the semiconductor substrate 10 with the coating film formed thereon) and the ultraviolet light 34 is irradiated through the partition wall 33 to the object. Accordingly, the influence of gases evolved from the object on the ultraviolet introduction part 32 can be suppressed by the partition wall 33. As a result, even ultraviolet light 34 can be irradiated to the object, and a scattering in properties of the film after annealing accompanied with ultraviolet photon irradiation can be eliminated.

Figure 18:
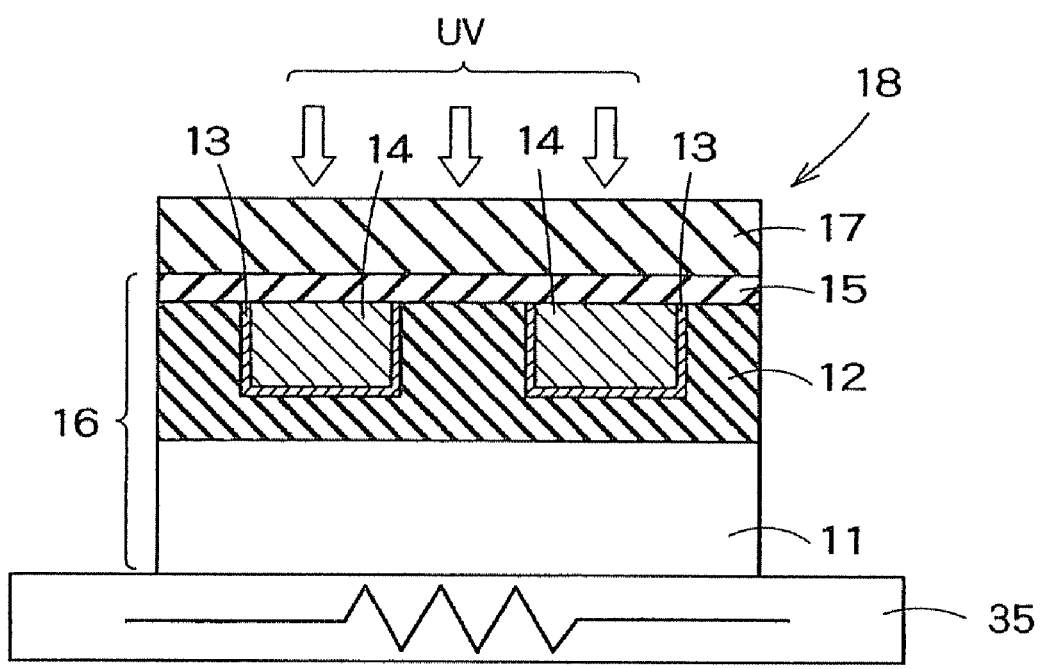
FIG. 18 is a schematic diagram showing a production process of a semiconductor device in a fourth embodiment.

Next, an example of the production of a semiconductor device using the ultraviolet photon irradiation apparatus will be described. FIG. 18 is a schematic diagram showing a production process of a semiconductor device in the fourth embodiment.

A first layer semiconductor substrate 16 is first produced in the same process as in the third embodiment.

As shown in FIG. 18, a low-k interlayer insulating film 17 consisted of a cyclobutane cross-linked organosilicon oxide film is then formed on the silicon nitride film 15 using the compositions for film formation described above in connection with the first embodiment. The step of forming the cyclobutane cross-linked organosilicon oxide film is performed basically in the same sequence as the steps 1 to 4 in the third embodiment. The fourth embodiment is different from the third embodiment only in that, unlike the step 4 in the third embodiment wherein electron beams are irradiated from the electron beam irradiation apparatus toward the varnish, in the fourth embodiment, ultraviolet light is irradiated instead of the electron beams.

The atmosphere, heating conditions and the like during energy beam, i.e. ultraviolet photon, irradiation may be the same as those in the third embodiment. When the wavelength of the ultraviolet light is set to from 120 nm to 400 nm while the total exposure dose of the ultraviolet light is set to not less than 1000 mJ/cm² and not more than 10000 mJ/cm², oxygen molecules contained in an ultraviolet photon irradiation atmosphere of the reaction vessel 31, or oxygen molecules dissolved in the varnish as the object for irradiation absorb ultraviolet photon energy and consequently are converted efficiently to reactive oxidants such as oxygen radicals or hydroxyl radicals. The reactive oxidant converts organic groups in the varnish (for example, organic groups such as an alkyl group contained in the cyclobutane cross-linkage composition) to silanol groups. In this case, all the organic groups are not converted to silanol groups, and the organic groups partially remain unconverted. Thereafter, a dehydration-condensation reaction between silanol groups occurs to form siloxane bond for cross-linking. Thus, an organosilicon oxide film can be formed. Further, upon the ultraviolet photon irradiation, a cross-linked structure can be formed in the organosilicon oxide film, whereby the mechanical strength, the interfacial adhesion, and the wettability can be improved.

Fifth Embodiment

The fifth embodiment of the present invention will be described with reference to the accompanying drawings. In this embodiment, an example of the formation of a cyclobutane cross-linked organosilicon oxide film by a plasma assist chemical vapor deposition method (a plasma CVD method) will be described.

Figure 19:
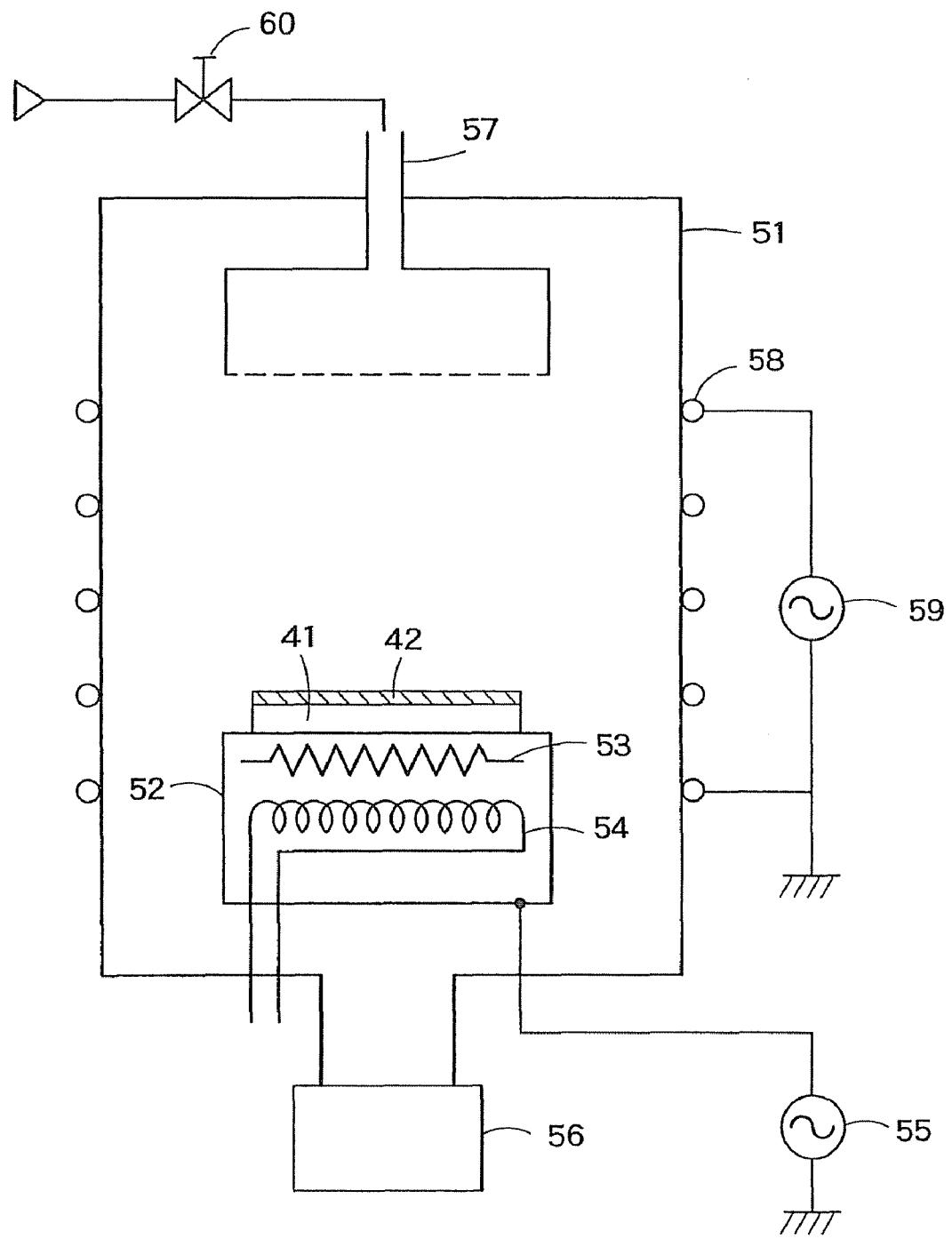
FIG. 19 is a schematic configuration diagram showing a high-density plasma CVD apparatus using helicon waves induction plasma that is used in a fifth embodiment.

Prior to the description of this embodiment, a plasma CVD apparatus used in this embodiment will be described. FIG. 19 is a schematic configuration diagram of a high-density plasma CVD apparatus using helicon waves that is used in this embodiment.

As shown in FIG. 19, the plasma CVD apparatus comprises a film deposition chamber 51 (a reaction vessel) made of an insulating material. A substrate support base 52, on which a semiconductor substrate 41 with semiconductor devices formed thereon is placed, is provided within the film deposition chamber 51. A resistive heating heater 53 as an internal heater and a cooling pipe 54 for circulating a coolant are provided on the substrate support base 52. A high-frequency power supply 55 is connected to the substrate support base 52.

An evacuation device 56 is provided at lower part of the film deposition chamber 51, whereby the internal pressure of the film deposition chamber 51 can be held on a suitable level. A nozzle 57 for introducing a source gas into the film deposition chamber 51 is provided at the upper part of the film deposition chamber 51. A high-frequency induction coil 58 is wound around the side wall of the film deposition chamber 51, and a high-frequency power supply 59 is connected to the high-frequency coil 58.

A gate valve 60 for regulating the flow rate of the source gas is connected through a pipe to the nozzle 57. For simplification, only one system is shown for the source gas introduction part such as a gate valve. In fact, however, the source gas introduction part is provided for each source gas.

Next, the method for cyclobutane cross-linked organosilicon oxide film formation using the plasma CVD apparatus will be described.

A semiconductor substrate 41 with semiconductor devices formed thereon is placed on a substrate support base 52. The temperature of the substrate is set to a predetermined temperature (a heating temperature) by a resistive heater 53. The substrate temperature is set to 400° C. or above (for example, 430° C.) at which, in thermal desorption spectroscopy (TDS) which has been previously performed, dehydrocondensation reaction of so-called constitution water species (i.e. Si—OH, HOH) incorporable into SiO₂ proceeds significantly.

Next, the cyclobutane cross-linkage composition gas described above as a source gas in connection with the first embodiment, an O₂ gas, and an argon (Ar) gas or a nitrogen (N₂) gas for dilution and carrier are simultaneously introduced, into the film deposition chamber 51, under the flow rates of 50 cm³/min, 500 cm³/min, and 500 cm³/min respectively, and the total pressure kept at 133 Pa in the film deposition chamber 51.

Next, a radio frequency (RF) electric power of 13.56 MHz is applied by the high-frequency power supply 59 to the high-frequency induction coil 58 on the side wall of the film deposition chamber 51 in order to start discharge. At the same time, an RF bias of 350 kHz (500 W) is applied by the high-frequency power supply 55 to the substrate support base 52. Thus, a cyclobutane cross-linked organosilicon oxide film 42 is formed on the semiconductor substrate 41. In this film formation process, preferably, electrons or ions (typically O± and O₂± ions) having an energy high enough to deposit an energy of not less than from about 12 to 25 eV to the surface of a cyclobutane cross-linked organosilicon oxide film 43 during film formation are also irradiated. Upon the irradiation of such electrons or ions, O—H bonds in both Si—OH and H—OH incorporable into the cyclobutane cross-linked organosilicon oxide film 42 can be broken, and the dehydrocondensation reaction of Si—OH on the film surface can be promoted to densify an SiO₂ network.

Sixth Embodiment

The sixth embodiment of the present invention will be described with reference to the accompanying drawings. In this embodiment, an example of the production of a cyclobutane cross-linked organosilicon oxide film using a plasma CVD method which is different from that used in the fifth embodiment will be described.

Figure 20:
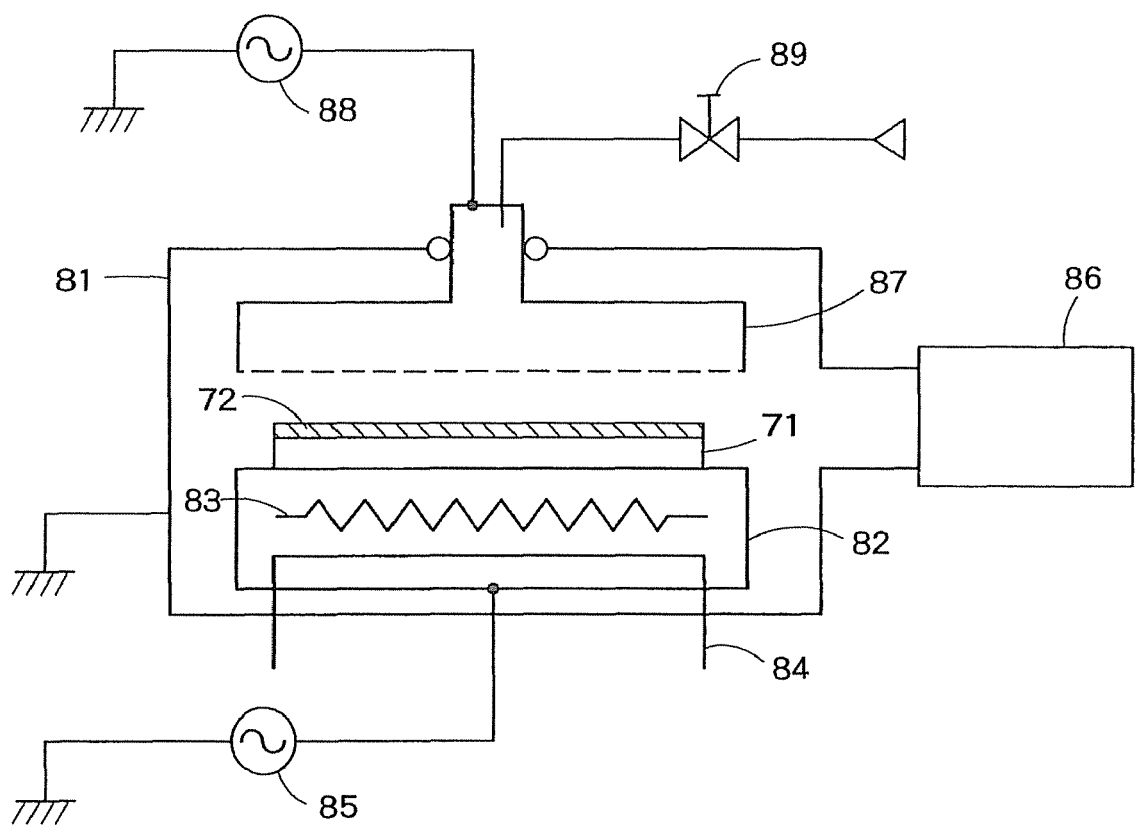
FIG. 20 is a schematic configuration diagram showing a dual-frequency parallel-plate type plasma CVD apparatus that is used in a sixth embodiment.

Prior to the description of this embodiment, a plasma CVD apparatus used in this embodiment will be described. FIG. 20 is a schematic configuration diagram showing a parallel plate type plasma CVD apparatus that is used in the sixth embodiment.

As shown in FIG. 20, the plasma CVD apparatus comprises a film deposition chamber 81 (a reaction vessel) made of an insulating material. A substrate support base 82, on which a semiconductor substrate 71 with semiconductor devices formed thereon is placed, is provided within the film deposition chamber 81. A resistive heater 83 as an internal heater and a cooling pipe 84 for circulating a coolant are provided on the substrate support base 82. A high-frequency power supply 85 is connected to the substrate support base 82.

An evacuation device 86 is provided on the side part of the film deposition chamber 81, whereby the inside of the film deposition chamber 81 can be evacuated and, at the same time, the pressure within the film deposition chamber 81 can be held on a suitable level. An electrode 87, which functions also as a nozzle for introducing a source gas into the film deposition chamber 81, is provided at the upper part of the film deposition chamber 81. A high-frequency power supply 88 is connected to the electrode 87.

A gate valve 89 for regulating the flow rate of the source gas is connected through a pipe to the electrode 87. For simplification, only one system is shown for the source gas introduction part such as the gate valve. In fact, however, the source gas introduction part is provided for each source gas.

Next, the method for cyclobutane cross-linked organosilicon oxide film formation using the plasma CVD apparatus will be described.

A semiconductor substrate 71 with semiconductor devices formed thereon is placed on a substrate support base 82. The temperature of the substrate 71 is set to a predetermined temperature (a heating temperature) by a resistive heater 83. The substrate temperature is set to 400° C. or above (for example, 430° C.) at which dehydrocondensation reaction of so-called constitution water (i.e. Si—OH, HOH) incorporable into $SiO_2$ proceeds significantly.

Next, the cyclobutane cross-linkage composition gas described above as a source gas in connection with the first embodiment, an $O_2$ gas, and an argon (Ar) gas or a nitrogen ($N_2$) gas for dilution and carrier are simultaneously introduced, into the film deposition chamber 81, under the flow rates of 50 cm³/min, 500 cm³/min, and 500 cm³/min respectively, and the total pressure kept at 133 Pa within the film deposition chamber 81.

Next, a radio frequency (RF) electric power of 13.56 MHz (1 kW) is applied by the high-frequency power supply 88 to the electrode 87 in order to start discharge. At the same time, an RF bias of 350 kHz (500 W) is applied by the high-frequency power supply 85 to the substrate support base 82. Thus, a cyclobutane cross-linked organosilicon oxide film 72 is formed on the semiconductor substrate 71. In this film formation process, preferably, electrons or ions (typically $O^\pm$ and $O_2^\pm$ ions) having an energy high enough to deposit an energy of not less than about 12 eV to the surface of a cyclobutane cross-linked organosilicon oxide film 72 during film formation are also irradiated. Upon the irradiation of such electrons or ions, O—H bonds in both Si—OH and H—OH incorporable into the cyclobutane cross-linked organosilicon oxide film 72 can be broken, and the dehydrocondensation reaction of Si—OH on the film surface can be promoted to densify an $SiO_2$ network.

In the fifth and sixth embodiments, examples of use of a plasma CVD apparatus using helicon waves and a parallel plate type plasma CVD apparatus as the plasma CVD apparatus are described. Other CVD apparatuses may be used. Even when CVD apparatuses, which can produce plasma having a high plasma density of not less than $1\times10^{11}$ ions/cm³, for example, microwave discharge and magnetron discharge, for example, plasma CVD apparatuses utilizing cyclotron resonance, plasma CVD apparatuses using an induction current, dipole ring magnetron plasma CVD apparatuses, or magnetron parallel plate CVD apparatuses are used, cyclobutane cross-linked organosilicon oxide films as described in the fifth and sixth embodiments can be formed by regulating conditions of plasma discharge, discharge pressure, and other process parameters during the insulating film formation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Example

The present invention is further illustrated by the following Example. In the Example, % is weight % unless otherwise specified.

In the Example, the dielectric constant, Young's modulus, cracking resistance, and resistance against $O_2$ plasma treatment are evaluated for organosilicon oxide films formed using a cyclobutane cross-linkage composition. In addition, in order to compare the film properties with those of the organosilicon oxide films formed using only the cyclobutane cross-linkage composition, several kinds of films are adopted comprised of the mixture of the cyclobutane cross-linkage composition and an ethylene cross-linkage composition with several mixing ratio up to the ethylene cross-linkage composition alone.

(Synthetic Process)

Cyclobutane Cross-Linkage Composition 1,2-Bis(tri-ethoxysilyl)acetylene represented by formula (A) was mixed with 1.2 mol equivalent of zirconocene diethyl, and the mixture was stirred at room temperature for one hr. Subsequently, 1.2 mol equivalent of iodine was mixed thereinto, and the mixture was stirred at 0° C. for 2 hr. Finally, 1.2 mol equivalent of copper(I) chloride was mixed thereinto, and the mixture was stirred at room temperature for 6 hr. Thus, the reactions were successively performed. Thereafter, the reaction solution was filtered to remove salts. The filtrate was then concentrated under the reduced pressure, and the concentrate was purified by column chromatography on alumina to give 1,2-bis(tri-ethoxysilyl)cyclobutene as a substituted position isomer mixture at a yield of 60%. In the reaction with copper(I) chloride, the yield of bis(tri-ethoxysilyl)cyclobutene when 0.1 mol equivalent of copper(I) chloride was mixed followed by stirring at room temperature for 24 hr was identical to the yield of bis(tri-ethoxysilyl)cyclobutene when 0.1 mol equivalent of copper(I) chloride was mixed followed by stirring at 50° C. for 6 hr. Subsequently, a hydrogenation reaction is performed to give 1,2-bis(tri-ethoxysilyl)cyclobutane (I-1).

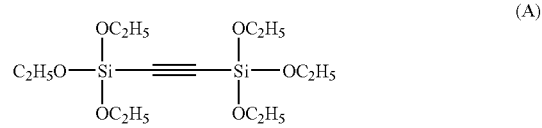

(A)

Ethylene Cross-Linkage Composition

Bis(monomethyl.dimethoxy)siloxane ethane represented by formula (B) is dissolved in 7 ml of propylene glycol monopropyl ether. A 0.4% aqueous nitric acid solution (200 mg) is added to the solution, and the mixture is stirred for 12 hr. The mixture is then concentrated under the reduced pressure to g (mass of the liquid) and thus to give an ethylene cross-linkage composition (B-1) as a comparative composition.

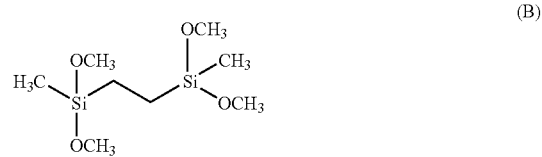

(B)

(Method for Film Formation)

The cyclobutane cross-linkage composition (I-1) and/or the ethylene cross-linkage composition (B-1) are dissolved in propylene glycol monoethyl ether to give a liquid chemical which is called a vanish in the previous embodiments. The liquid chemical is spin coated onto a 300 mm silicon wafer as a substrate. The coated substrate is then dried on a hot plate at 80° C. for one min and at 200° C. for one min and further is heated in a clean oven under a dry nitrogen atmosphere having an oxygen concentration as a partial pressure of not more than 500 ppm at 380° C. for 20 min to from an organosilicon oxide film (Evaluation Method)

The dielectric constant, Young's modulus, cracking resistance, and resistance against $O_2$ plasma treatment are evaluated for the organosilicon oxide film formed above. The dielectric constant can be determined by preparing an MIS capacitor and measuring the film thickness and capacitance-voltage (C-V) characteristics. The Young's modulus (film mechanical strength) can be measured with Nano Indenter XP manufactured by MTS Systems Corporation. The minimum film thickness necessary for the measurement is 300 nm. When the film thickness is smaller than 300 nm, there is a possibility that accurate values cannot be determined due to the influence of the Si substrate.

Regarding the cracking resistance, various organosilicon oxide films having different film thicknesses are exposed to the atmospheric air for one day and are then inspected for the presence of cracking on the surface of the organosilicon oxide films by an oblique lightening method. In this case, the cracking resistance can be expressed in terms of the maximum film thickness free from cracking. Regarding the resistance against $O_2$ plasma treatment, the formed organosilicon oxide film is exposed to an $O_2$ plasma for one min to deteriorate the surface of the organosilicon oxide film followed by dissolution of the deteriorated layer in a hydrofluoric acid solution (1 wt %). The thickness of the film dissolved in the hydrofluoric acid solution can be regarded as the thickness of a deteriorated layer formed by $O_2$ plasma treatment. The thickness of the deteriorated layer significantly varies depending upon plasma treatment conditions. Reactive ion etching (RIE) using $O_2$ gas, which has moderate deterioration rate of the surface, is used to evaluate accurately the thickness of the deteriorated layer.

(Evaluation Results)

The dielectric constant and Young's modulus of the films without deterioration treatments are shown in Table 2.

TABLE 2

| Composition ratio (I-1)/(B-1) | Dielectric constant | Young's modulus (GPa) |
|---|---|---|
| 0/100 | 2.65 | 4.5 |
| 30/70 | 2.48 | 6.3 |
| 100/0 | 2.41 | 7.0 |

It can be confirmed from Table 2 that a reduction in dielectric constant and an improvement in Young's modulus can be realized in the above composition range of the cyclobutane cross-linkage composition (I-1) to the ethylene cross-linkage composition (B-1), indicating that the organosilicon oxide film using the cyclobutane cross-linkage composition according to the present invention has excellent properties such as a low dielectric constant and a high mechanical strength.

Figure 21:
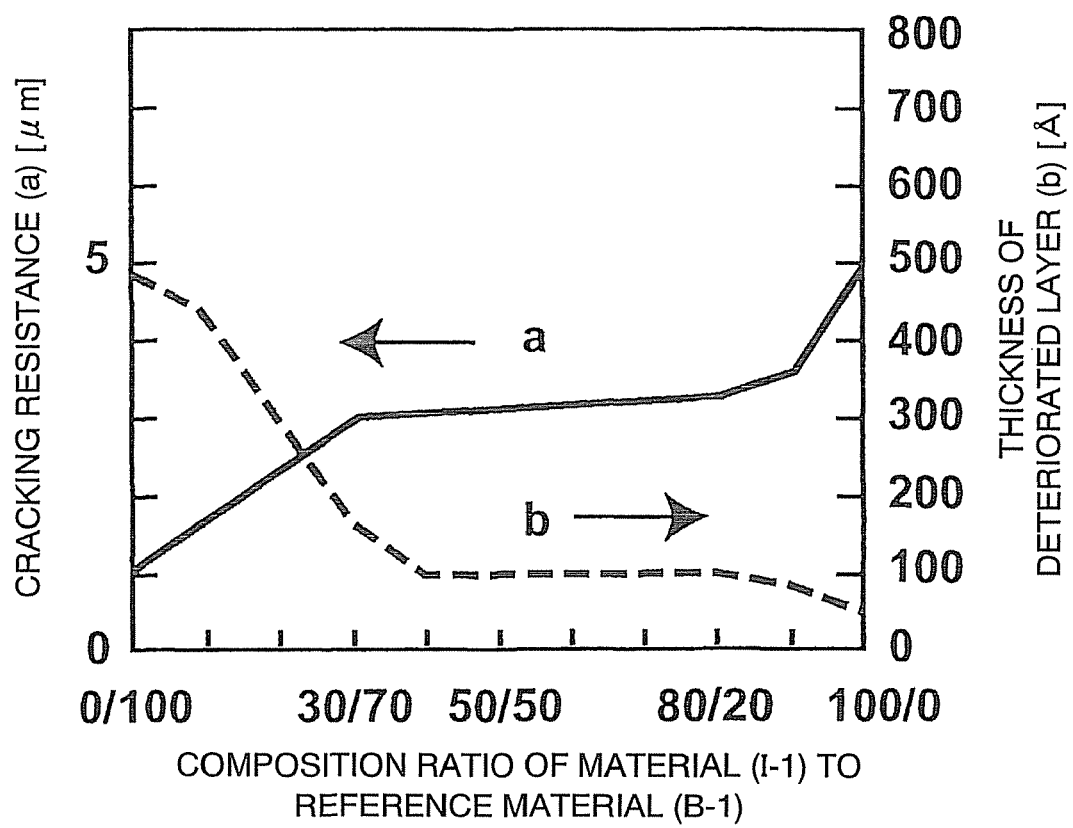
FIG. 21 is a graph showing a relationship of both cracking resistance of an organosilicon oxide film and the thickness of a deteriorated layer formed after plasma treatment with a mixing ratio between a cyclobutane-linkage composition (I-1) and an ethylene-linkage composition (B-1).

The relationship of the mixing ratio (weight ratio) between the cyclobutane cross-linkage composition (I-1) and the ethylene cross-linkage composition (B-1) with the cracking resistance of the organosilicon oxide film and with the thickness of the deteriorated layer formed by the plasma treatment is shown in FIG. 21. In the graph shown in FIG. 21, a notation "a" represents cracking resistance, and a notation "b" represents the thickness of the deteriorated layer. When the mixing ratio (weight ratio) of the cyclobutane cross-linkage composition (I-1) to the ethylene cross-linkage composition (B-1) is in the range of from 30/70 to 100/0, the cracking resistance is 3 mm. Further, when the mixing ratio is in the range of from 40/60 to 100/0, the thickness of the deteriorated layer can be suppressed to not more than 10 nm. In the organosilicon oxide film for the interlayer insulating film, the higher the cracking resistance, the better it works. In this case, the thickness of the deteriorated layer should be not more than 10 nm. When only the ethylene cross-linkage composition (B-1) is used, a deteriorated layer having a thickness of 50 nm is formed. The reason for this is as follows. The organosilicon oxide film has large gaps (pores) and thus is not uniform. Consequently, when the organosilicon oxide film is exposed to $O_2$ plasma, O radicals penetrate into the organosilicon oxide film, and react with —$CH_3$, —$CH_2$ and other groups, and then etch off them to form a deteriorated layer. On the other hand, when the cyclobutane cross-linkage composition is used as in this Example, the size of gaps (pores) is so small enough that the film is homogenized to prevent the penetration of O radicals and, consequently, the thickness of the deteriorated layer can be reduced. The application of N/H plasma treatment instead of $O_2$ plasma treatment can also suppress the deterioration in both the properties and is more suitable for practical plasma treatment process than the $O_2$ plasma treatment. However, the same tendency toward the improvement still can be realized and effective by using the cyclobutane cross-linkage composition (I-1). Further, it can be confirmed that the cracking resistance of the organosilicon oxide film is improved through the suppression of the penetration of hygroscopic moisture from external ambient by virtue of small gaps (pores).

The invention claimed is:

1. A composition for film formation, comprising a compound represented by general formula (I) or a hydrolyzed-dehydrocondensation product thereof:

$$X^1{}_{3-m}R^1{}_mSiR^2SiR^3{}_nX^2{}_{3-n} \qquad (I)$$

wherein $R^1$ and $R^3$ represent a hydrogen atom or a monovalent substituent; $R^2$ represents a divalent group having an alicyclic structure with four carbon atoms or a derivative of the divalent group; $X^1$ and $X^2$ represent a hydrolysable group; and m and n are an integer of from 0 to 2.

2. The composition according to claim 1, wherein the divalent group represented by $R^2$ in general formula (I) represents cyclobutane (—$C_4H_6$—), cyclofluorobutane (—$C_4H_{6-X}F_X$—), cyclopolymethylbutane (—$C_4H_{6-X}(CH_3)_X$—), cyclopolymethylfluorobutane (—$C_4H_{6-Y-Z}(F_Y(CH_3)_Z)$—), cyclochlorobutane (—$C_4H_{6-X}Cl_X$—), or cyclopolymethylchlorobutane (—$C_4H_{6-Y-Z}(Cl_Y(CH_3)_Z)$—) wherein X is an integer of from 1 to 6; and Y and Z are an integer of from 1 to 5 and satisfy a relationship of $2 \leq Y+Z \leq 6$.

3. The composition according to claim 2, wherein the divalent group represented by $R^2$ in general formula (I) has an alicyclic structure (—$C_4X_6$—) skeleton with four carbon atoms, and Si in general formula (I) is at ortho-position or para-position of the alicyclic structure and is bonded to the alicyclic structure to constitute a trans or gauche form.

4. The composition according to claim 1, wherein m and n in general formula (I) satisfy $m+n \geq 1$.

5. The composition according to claim 4, wherein m and n in general formula (I) are 1.

6. The composition according to claim 1, which further comprises a compound represented by general formula (II) or a hydrolyzed-dehydrocondensation product thereof:

$$R^4{}_pSiX^3{}_{4-p} \qquad (II)$$

wherein $R^4$ represents a hydrogen atom or a substituent; $X^3$ represents a hydrolysable group; and p is an integer of from 0 to 3.

7. An insulating film comprising an organosilicon oxide film having a single composition or a mixed composition produced using at least a composition for film formation according to claim 1.

8. The insulating film according to claim 7, wherein the ratio between the number of cross-linkage groups $R^2$s and the number of Si atoms, i.e., $R^2$/Si, is not less than 0.5 and not more than 2.

9. A semiconductor device comprising an organosilicon oxide film according to claim 7.

10. A process for producing a semiconductor device comprising an organosilicon oxide film according to claim 7, wherein
the organosilicon oxide film is formed by a process comprising:
forming a film using a composition for film formation according to claim 1, by a coating method or a plasma enhanced chemical vapor deposition method;
heat treating the film in an oxidizing atmosphere; and
heat treating the heat-treated film in a non-oxidizing atmosphere.

11. The process according to claim 10, wherein the film is heat-treated at 200° C. or above and 350° C. or below in the oxidizing atmosphere and the heat-treated film is heat-treated at 400° C. or above and 600° C. or below in the non-oxidizing atmosphere.

12. A process for producing a semiconductor device comprising an organosilicon oxide film according to claim 7, wherein
the organosilicon oxide film is formed by a process comprising:
forming a film using a composition for film formation according to claim 1, by a coating method or a plasma enhanced chemical vapor deposition method; and
irradiating the film with an energy beam while heat treatment of the film under a reduced pressure compared with an atmospheric pressure.

13. The process according to claim 12, wherein the heat treatment is carried out under a pressure of not less than 0 Pa and not more than $5.5 \times 10^4$ Pa, and is carried out at 200° C. or above and 500° C. or below.

14. The process according to claim 12, wherein the energy beam is an electron beam or an ultraviolet photon.

* * * * *